United States Patent [19]

Moriyasu et al.

[11] Patent Number: 5,352,655

[45] Date of Patent: Oct. 4, 1994

[54] 3-AZABICYCLO[3.1.0]HEXANE-2-ONE DERIVATIVES AND HERBICIDAL COMPOSITIONS CONTAINING THEM AS HERBICIDALLY ACTIVE INGREDIENTS

[75] Inventors: Koichi Moriyasu; Kanji Tomiya; Hideyuki Akieda; Harumichi Aoki; Makoto Suzuki; Yasunaga Iwasaki; Sadafumi Koda, all of Mobara, Japan

[73] Assignee: Mitsui Toatsu Chemicals, Incorporated, Tokyo, Japan

[21] Appl. No.: 161,478

[22] Filed: Dec. 6, 1993

[30] Foreign Application Priority Data

Dec. 4, 1992 [JP] Japan .................. 4-325433
Feb. 2, 1993 [JP] Japan .................. 5-015140

[51] Int. Cl.$^5$ ............................ C07D 209/52
[52] U.S. Cl. .................. 504/285; 548/512
[58] Field of Search ............. 548/512; 504/285

[56] References Cited

U.S. PATENT DOCUMENTS 3,745,170  7/1973  Fujinami et al. .
4,082,849  4/1978  Kameda et al. .
4,118,393  10/1978  Fanshawe et al. .
4,196,120  4/1980  Fanshawe et al. .

FOREIGN PATENT DOCUMENTS 0004107  9/1979  European Pat. Off. .

OTHER PUBLICATIONS

Chemical Abstracts, vol. 103, pp. 342-343, 1985, AN-11523u.
CA89:6216j Analgesic azabicyclohexanes, Fanshawe et al., p. 532, 1978.
CA99:22310x Azabicyclohexanes, Epstein et al., p. 604, 1983.
CA101:38344g Treating . . . azabicyclohexanes. Epstein et al., p. 499, 1984.

*Primary Examiner*—Johann Richter
*Assistant Examiner*—Joseph K. McKane
*Attorney, Agent, or Firm*—Oblon, Spivak, McClelland, Maier & Neustadt

[57] ABSTRACT

A 3-azabicyclo[3.1.0]hexane-2-one derivative represented by the following formula (I), and a herbicidal composition containing the same as a herbicidally active ingredient:

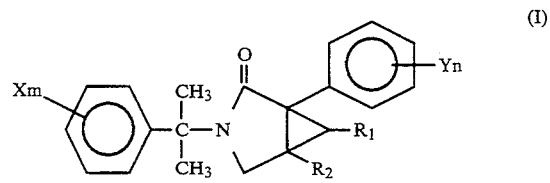

(I)

(wherein X is a halogen atom, an alkyl group having 1 to 3 carbon atoms, an alkoxy group having 1 to 3 carbon atoms or a haloalkyl group having 1 to 3 carbon atoms; Y is a halogen atom or an alkyl group having 1 to 3 carbon atoms; $R_1$ is a hydrogen atom or an alkyl group having 1 to 3 carbon atoms; $R_2$ is a hydrogen atom or an alkyl group having 1 to 3 carbon atoms; m is an integer of 0 to 3; n is an integer of 0 to 2; and when m is 2 or 3, the groups represented by X may be identical or different, and when n is 2, the groups represented by Y may be identical or different).

10 Claims, No Drawings

3-AZABICYCLO[3.1.0]HEXANE-2-ONE DERIVATIVES AND HERBICIDAL COMPOSITIONS CONTAINING THEM AS HERBICIDALLY ACTIVE INGREDIENTS

BACKGROUND OF THE INVENTION (i) Field of the Invention

The present invention relates to 3-azabicyclo-[3.1.0]hexane-2-one derivatives and herbicidal compositions containing them as herbicidally active ingredients.

(ii) Description of the Prior Art

In U.S. Pat. No. 3,745,170, it is described that certain kinds of 3-azabicyclo[3.1.0]hexane derivatives show a sterilizing activity. A typical compound mentioned in this publication, 1,5-dimethyl-3-(3,5-dichlorophenyl)-3-azabicyclo[3.1.0]hexane-2,4-dione (general name: procymidone) is commercially available as a gray mold disease inhibitor. Furthermore, in Journal of Chromatography, Vol. 318(2), pp. 398–403 (1985), there is mentioned 3-ethyl-1-phenyl-3-azabicyclo[3.1.0]hexane-2-one, but reports regarding a herbicidal activity are not present. In addition, U.S. Pat. Nos. 4,118,393 and 4,196,120 disclose 3-benzyl-1-phenyl-3-azabicyclo[3.1.0]hexane-2,4-dione derivatives as an antidepressant and its synthetic intermediate, but reports regarding the herbicidal activity are not present.

In recent years, a herbicidal composition having a high selectivity is strongly desired which has no injurious action on crops and which can exterminate weeds alone. Furthermore, for paddy fields, an effective herbicidal composition is desired which can securely control hardly eliminable weeds such as barnyardgrass (Echinochloa), bulrush (*Scirpus juncoides*), monochroria (*Monochoria vaginalis*) and water nutgrass (*Cyperus serotinus*). In addition, it is strongly required to develop a herbicidal composition which is usable in an optional term of from the pre-emergence of weeds to the growing period of the emerged weeds and which maintains the herbicidal effect for a long period of time.

In consequence, the present invention intends to provide a selective herbicidal composition which has no injurious action on rice plants in paddy fields, has a wide herbicidal spectrum in a low application rate, and can be used in a prolonged term of from the pre-emergence of weeds to the growing period of the emerged weeds.

SUMMARY OF THE INVENTION

The present inventors have conducted research about 3-azabicyclo[3.1.0]hexane-2-one derivatives with the intention of solving the above-mentioned problems, and as a result, they have found that novel 3-azabicyclo[3.1.0]hexane-2-one derivatives having a specific phenyl group at the 1-position of a 3-azabicyclo[3.1.0]hexane ring and an α,α-dimethyl-substituted benzyl group at the 3-position of the same ring are extremely excellent as herbicidal compositions, and what is better, these derivatives have no injurious action on rice plants which are useful crops.

That is, the present invention is directed to 3-azabicyclo[3.1.0]hexane-2-one derivatives represented by the formula (I)

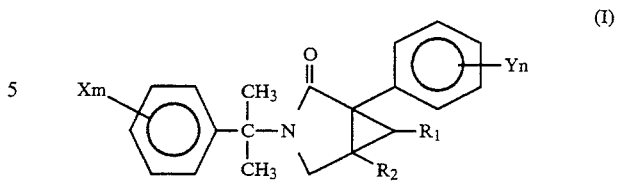

(wherein X is a hydrogen atom, a halogen atom, an alkyl group having 1 to 3 carbon atoms, an alkoxy group having 1 to 3 carbon atoms or a haloalkyl group having 1 to 3 carbon atoms; Y is a hydrogen atom, a halogen atom or an alkyl group having 1 to 3 carbon atoms; $R_1$ is a hydrogen atom or an alkyl group having 1 to 3 carbon atoms; $R_2$ is a hydrogen atom or an alkyl group having 1 to 3 carbon atoms; m is an integer of 1 to 3; n is an integer of 1 or 2; and when m is 2 or 3, the groups represented by X may be identical or different, and when n is 2, the groups represented by Y may be identical or different), and herbicidal compositions characterized by containing these derivatives as herbicidally active ingredients.

DETAILED DESCRIPTION OF THE INVENTION

Compounds represented by the formula (I) of the present invention are novel, and in this formula (I), examples of a halogen atom include fluorine, chlorine, bromine and iodine. Examples of an alkyl group having 1 to 3 carbon atoms include methyl, ethyl, n-propyl and iso-propyl. Examples of an alkoxy group having 1 to 3 carbon atoms include methoxy, ethoxy, n-propoxy and iso-propoxy, and examples of a haloalkyl group having 1 to 3 carbon atoms include difluoromethyl, trifluoromethyl, pentafluoroethyl and tetrafluoroethyl.

A preferable example of the compounds represented by the formula (I) regarding the present invention is a compound in which $R_1$ is a hydrogen atom, $R_2$ is a methyl group, Yn is a hydrogen atom or a fluorine atom substituted at the 2-position, and at least one of X is a halogen atom substituted at the 3-position.

The 3-azabicyclo[3.1.0]hexane-2-one derivative of the present invention is a novel compound, and it can be prepared by the following process shown by the reaction formula (1):

Reaction Formula (1)

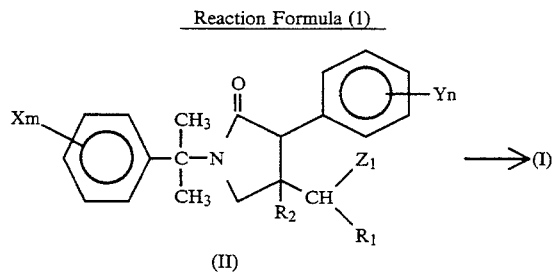

That is, the 3-azabicyclo[3.1.0]hexane-2-one derivative can be prepared by treating a pyrrolidinone derivative represented by the formula (II) (wherein X is a hydrogen atom, a halogen atom, an alkyl group having 1 to 3 carbon atoms, an alkoxy group having 1 to 3 carbon atoms or a haloalkyl group having 1 to 3 carbon atoms; Y is a hydrogen atom, a halogen atom or an alkyl group having 1 to 3 carbon atoms; $R_1$ is a hydrogen atom or an alkyl group having 1 to 3 carbon atoms; $R_2$ is a hydrogen atom or an alkyl group having 1 to 3 carbon atoms; $Z_1$ is a halogen atom; m is an integer of 1 to 3; n is an integer of 1 or 2; and when m is 2 or 3, the groups represented by X may be identical or different, and when n is 2, the groups represented by Y may be identical or different) with a suitable base to carry out an intramolecular alkylation reaction.

Examples of the suitable base which can be used in this reaction include hydroxides of alkaline metals such as sodium hydroxide, potassium hydroxide and lithium hydroxide, hydroxides of alkaline earth metals such as calcium hydroxide and barium hydroxide, alkaline metals such as metallic sodium, metallic potassium and metallic lithium, metal hydrides such as sodium hydride and lithium hydride, alcolates such as t-butoxypotassium and sodium alkoxide, aliphatic amines such as methylamine, ethylamine, dimethylamine, diethylamine and triethylamine, aromatic amines such as aniline and N,N-dimethylaniline, organic bases such as pyridine, picoline, quinoline and 1,8-diazabicyclo[5.4.0]-undec-7-ene (DBU).

This reaction can be carried out in a suitable solvent or in the absence of any solvent. Examples of the suitable solvent include aromatics such as benzene, toluene and xylene, ethers such as dioxane, tetrahydrofuran and diethyl ether, esters such as ethyl acetate and butyl acetate, lower alcohols such as methanol, ethanol, propanol and butanol, and non-protonic polar solvents such as dimethylformamide. A reaction temperature is in the range of from $-70°$ to $160°$ C., and the reaction may be carried out at a reflux temperature of the above-mentioned solvent.

The pyrrolidinone derivative represented by the formula (II) can be prepared by a process shown by the reaction formula (2):

Reaction Formula (2)

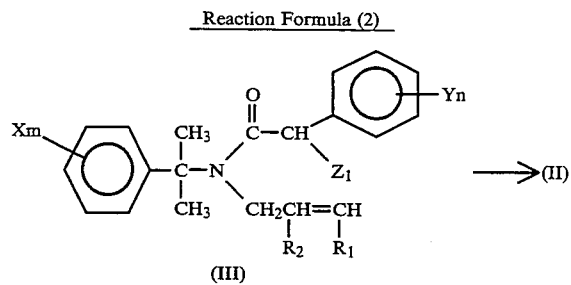

(III)

That is, the pyrrolidinone derivative can be prepared by subjecting an amide derivative represented by the formula (III) (wherein X, Y, $R_1$, $R_2$, m, n and $Z_1$ are as defined above) to a cyclization reaction in the presence of a suitable catalyst.

The suitable catalyst is a transition metal catalyst, i.e., a catalyst which can generate ferrous ions or cuprous ions. Typical examples of such a catalyst are preferably ferrous chloride and cuprous chloride. The reaction is preferably carried out in a solvent, and this solvent is preferably that which does not disturb the reaction. That is, typical examples of the preferable solvent include diethylene glycol dimethyl ether, dimethylacetamide, dimethyl sulfoxide, acetonitrile, and aromatics such as benzene, cumene, xylene and toluene. Furthermore, in order to accelerate the reaction, it is also effective to carry out the reaction in the presence of an amine. A reaction temperature is in the range of from $20°$ to $190°$ C., preferably from $70°$ to $150°$ C.

The amide derivative represented by the formula (III) can be prepared in accordance with a process shown by the reaction formula (3):

Reaction Formula (3)

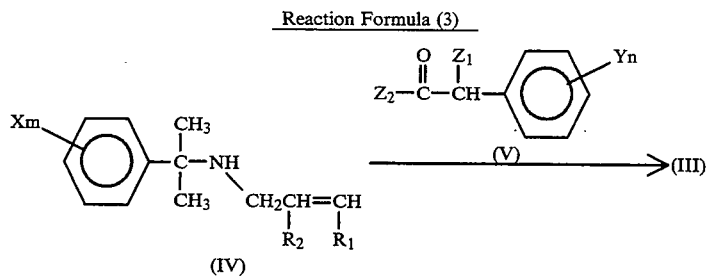

That is, the amide derivative can be prepared by reacting a secondary amine derivative represented by the formula (IV) with a carboxylic acid derivative represented by the formula (V) (wherein X, Y, $R_1$, $R_2$, m, n and $Z_1$ are as defined above, and $Z_2$ is a halogen atom).

The reaction can be carried out in the absence of any solvent or in a suitable solvent. Examples of the suitable solvent include aromatics such as benzene, toluene, xylene, chlorobenzene and dichlorobenzene, halogenated hydrocarbons such as dichloromethane, chloroform and carbon tetrachloride, ethers such as diethyl ether, tetrahydrofuran and dioxane, and esters such as ethyl acetate and butyl acetate. The reaction proceeds at an optional temperature, and it is also effective to carry out the reaction in the presence of a base such as triethylamine, pyridine, dimethylaniline, sodium hydride and potassium hydride, sodium carbonate, potassium carbonate and sodium hydrogencarbonate.

The secondary amide derivative represented by the formula (IV) can be prepared by reacting an α,α-dimethylbenzylamine derivative with a halogenated alkenyl derivative, and the carboxylic acid derivative represented by the formula (V) can be prepared from a mandelic acid derivative or a phenylacetic acid derivative by a known process.

Furthermore, 1-methyl-1-[3-(1-methylethyl)phenyl]ethylamine as a raw material of the compound of the present invention in which Xm is an isopropyl group substituted at the 3-position is a novel compound and can be prepared by the reaction formula (4):

Reaction Formula (4)

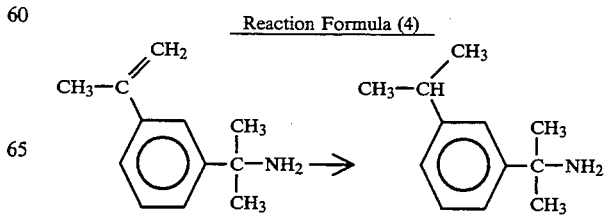

That is, 1-methyl-1-[3-(1-methylethyl)phenyl]ethylamine can be prepared by subjecting 1-methyl-1-[3-(1-methylethenyl)phenyl]ethylamine to a hydrogenation reaction in the presence of a suitable catalyst under a hydrogen gas stream. As the suitable catalyst, there can be used transition metal catalysts, i.e., platinum, palladium, rhodium and luthenium as well as oxides thereof.

The reaction can be carried out in the absence of any solvent or in a suitable solvent. Examples of the suitable solvent include lower alcohols such as methanol, ethanol, propanol and butanol, aromatics such as benzene, toluene and xylene, ethers such as diethyl ether, tetrahydrofuran and dioxane, esters such as ethyl acetate and butyl acetate, and non-protonic polar solvents such as dimethylformamide and dimethylacetamide. A reaction temperature is in the range of from 0° to 150° C., preferably from 15° to 100° C.

The compound in the reaction formula (4), 1-methyl-1-[3-(1-methylethenyl)phenyl]ethylamine can be prepared by a process shown by a reaction formula (5):

Reaction Formula (5)

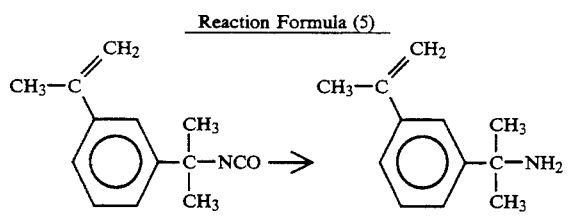

That is, 1-methyl-1-[3-(1-methylethenyl)phenyl]ethylamine can be prepared by hydrolyzing 1-methyl-1-[3-(1-methylethenyl)phenyl]ethyl isocyanate in the presence of a suitable base. Examples of the suitable base include hydroxides of alkaline metals such as potassium hydroxide, sodium hydroxide and lithium hydroxide, and hydroxides of alkaline earth metals such as calcium hydroxide and barium hydroxide.

Furthermore, this reaction may be carried out in a suitable solvent. Examples of the suitable solvent include lower alcohols such as methanol, ethanol, propanol and butanol, aromatics such as benzene, toluene and xylene, ethers such as dioxane, tetrahydrofuran and diethyl ether, esters such as ethyl acetate and butyl acetate, and non-protonic polar solvents such as dimethylformamide and dimethylacetamide.

Here, the compound in the reaction formula (5), 1-methyl-1-[3-(1-methylethenyl)phenyl]ethyl isocyanate is a known compound.

A herbicidal composition containing the thus obtainable compound represented by the formula (I) regarding the present invention as a herbicidally active ingredient has an excellent herbicidal effect to harmful weeds in most paddy fields, for example, gramineous weeds such as barnyard grass (Echinochloa) and the like, cyperaceous weeds such as *Cyperus microiria*, bulrush (*Sirpus juncoides*) and the like, annual broad leaf weeds such as monochoria (*Monochoria vaginalis*) and the like, and perennial weeds such as *Sagittaria pygmaea* and the like. On the other hand, the herbicidal composition has no injurious action on rice (*Oryza sativa*) which is an useful crop. Furthermore, the herbicidal composition of the present invention can be effectively used in all applications such as submerged soil application, soil application and soil incorporation in the long term of from the pre-emergence of weeds to the growing period of the developed weeds.

When the compound represented by the formula (I) regarding the present invention is used as a herbicidal composition, this compound is usually mixed with an inert liquid carrier or solid carrier, formulated in the form of powder, granules, wettable powder, emulsion, flowable formulation or the like, and then used. If required in the formulation, auxiliary agents can be added.

The carrier may be in the state of a solid or a liquid, and no particular restriction is put on the carrier, so long as it can be usually used in agents for agriculture and horticulture. Examples of the solid carrier include a mineral powder such as clay, talc, bentonite, calcium carbonate, diatomaceous earth and white carbon, vegetable powders such as a soybean powder and starch, and high polymer compounds such as petroleum resin, polyvinyl alcohol and polyalkylene glycols, urea and waxes. Furthermore, examples of the liquid carrier include various organic solvents such as xylene, methylnaphthalene and alkylbenzenes, various oils such as vegetable oils, and water.

Examples of the auxiliary agents include surfactants used in agents for agriculture and horticulture, binders (e.g., lignin sulfonic acid, alginic acid, polyvinyl alcohol, gum arabi and CMC sodium) and stabilizers (e.g., a phenolic compound, thiol compound or higher fatty acid ester is utilized for the prevention of oxidation, or a phosphate is utilized as a pH regulator, or in a certain case, a light stabilizer can also be used), and they can be used singly or in combination. In some cases, an industrial germicide or an antibacterial fungicide can be added for the control of bacteria and fungi.

Examples of the surfactant include non-ionic, anionic, cationic and amphoteric surfactants, which can be suitably used singly or in combination. A preferable example of the non-ionic surfactant can be obtained by adding ethylene oxide [e.g., Neugen EA80 (trade name made by Daiichi Kogyo Seiyaku Industries, Ltd.)] or propylene oxide to an alkylphenol, higher alcohol, alkylnaphthol, higher fatty acid, fatty acid ester or the like. A preferable example of the anionic surfactant is an alkylsulfonate salt [e.g., Neopelex (trade name, made by Kao Soap Co., Ltd.)], alkyl sulfate ester salt, phosphate ester salt or the like of an alkylphenol, alkylnaphthol, higher alcohol., higher fatty acid, fatty acid ester or the like. A lignine sulfonate salt [e.g., Sun Ekisu (trade name, made by Nippon Seishi Co., Ltd.] or the like is also one preferable example.

The content of the compound represented by the formula (I) in the herbicidal composition of the present invention depends upon the morphology of the formulation. In general, it is 0.01–20% by weight in a powder, 1–50% by weight in a wettable powder, 0.01–10% by weight in granules, 0.1–50% by weight in an emulsion, 0.1–50% by weight in a flowable formulation and 1–50% by weight in a dry flowable formulation. Preferably, it is 0.1–3% by weight in a powder, 10–40% by weight in a wettable powder, 0.1–5% by weight in granules, 1–30% by weight in an emulsion, 1–30% by weight in a flowable formulation and 10–40% by weight in a dry flowable formulation.

The content of the auxiliary agents is 0–80% by weight, and the content of the carrier is a value obtained by subtracting the content of the herbicidally active ingredient compound and the auxiliary agents from 100% by weight.

The herbicidal composition of the present invention containing the compound represented by the formula (I), needless to say, can be mixed with one or more of other herbicidal compositions or agricultural chemicals such as a fungicide, an insecticide and a plant growth regulator, a fertilizer, a soil improving agent and the like, and the herbicidal composition can also be prepared in the state of a mixed formulation therewith. In some cases, a synergistic effect can be expected from such a combination.

Next, a method for preparing compounds of the present invention will be described in detail in reference to examples. However, the scope of the present invention should not be limited to these examples.

EXAMPLE 1

Preparation of 3-[1-methyl-1-(3-chlorophenyl)ethyl]-5-methyl-1-(2-fluorophenyl)-3-azabicyclo[3.1.0]hexane-2-one To 20 ml of tetrahydrofuran were added 0.7 g of 1-[1-methyl-1-(3-chlorophenyl)ethyl]-4-bromomethyl-4-methyl-3-(2-fluorophenyl)pyrrolidine-2-one and 0.35 g of a 28% methanol solution of sodium methoxide, and the solution was then stirred at room temperature for 1 hour. After the solvent was distilled off, ice water was added to the solution, and extraction was then made with ethyl acetate. Next, the resultant extract was dried over anhydrous sodium sulfate, and after concentration, column chromatography was done to obtain 0.5 g of the desired 3-[1-methyl-1-(3-chlorophenyl)ethyl]-5-methyl-1-(2-fluorophenyl)-3-azabicyclo[3.1.0]hexane-2-one.

EXAMPLE 2

Preparation of 3-(1-methyl-1-phenylethyl)-1-(3-fluorophenyl)-3-azabicyclo[3.1.0]hexane-2-one To 15 ml of toluene were added 0.8 g of 1-(1-methyl-1-phenylethyl)-4-bromomethyl-3-(3-fluorophenyl)pyrrolidine-2-one and 0.4 g of 1,8-diazabicyclo[5.4.0]undec-7-ene (DBU), and the solution was then stirred at room temperature for 2 hours. After water was added to the solution, extraction was made with toluene, and the resultant extract was then dried over anhydrous sodium sulfate. After the solvent was distilled off, silica gel column chromatography was done to obtain 0.45 g of the desired 3-(1-methyl-1-phenylethyl)-1-(3-fluorophenyl)-3-azabicyclo[3.1.0]hexane-2-one.

EXAMPLE 3

Preparation of 3-[1-methyl-1-(3,5-dichlorophenyl)ethyl]-5-methyl-1-phenyl-3-azabicyclo[3.1.0]hexane-2-one First, 1.0 g of cuprous chloride and 1.3 g of di-n-butylamine were added at 100° C. to a solution formed by dissolving 1.3 g of N-[1-methyl-1-(3,5-dichlorophenyl)ethyl]-N-(2-methyl-2-propenyl)-2-chloro-2-phenylacetamide in 15 ml of toluene, and the solution was then stirred at a reflux temperature of 110° C. for 0.5 hour. After cooling, the reaction solution was poured into water, followed by filtration to separate an organic layer. Next, this organic layer was dried over anhydrous magnesium sulfate. After the solvent was distilled off, tetrahydrofuran was added to the solution to form 15 ml of a tetrahydrofuran solution, and 0.61 g of a 28% methanol solution of sodium methoxide was then added, followed by stirring at room temperature for 1 hour. After the solvent was distilled off, ice water was added to the solution, and extraction was made with ethyl acetate. The resultant organic layer was dried over anhydrous sodium sulfate, and after concentration, column chromatography was done to obtain 0.38 g of the desired 3-[1-methyl-1-(3,5-dichlorophenyl)ethyl]-5-methyl-1-phenyl-3-azabicyclo[3.1.0]hexane-2-one.

Other compounds represented by the formula (I) regarding the present invention were synthesized by the same procedures as in Example 1, 2 or 3. Physical properties of the synthesized compounds are shown in Table 1.

TABLE 1

| Compound No. | Substituents in formula (1) | | | | Physical properties |
|---|---|---|---|---|---|
| | Xm | Yn | $R_1$ | $R_2$ | |
| 1 | 3-Cl | 2-F | H | $CH_3$ | NMR (400MHz, $CDCl_3$) δppm: 1.11(3H, s), 1.18(1H, d, J=4.9Hz), 1.32(1H, d, J=4.9Hz), 1.67(3H, s), 1.69(3H, s), 3.51(1H, d, J=10.3Hz), 3.60(1H, d, J=10.3Hz), 7.00~7.30(8H, m) IR $\nu$KBr($cm^{-1}$): 1671 m.p. 105.5~107.0° C. |
| 2 | H | H | H | $CH_3$ | NMR (400MHz, $CDCl_3$) δppm: 1.08(3H, s), 1.11(1H, d, J=4.4Hz), 1.37(1H, d, J=4.4Hz), 1.74(3H, s), 1.77(3H, s), 3.36(1H, d, J=10.3Hz), 3.46(1H, d, J=10.3Hz), 7.18~7.38(10H, m) IR $\nu$KBr ($cm^{-1}$): 1676 m.p. 149.5~151.5° C. |
| 3 | H | H | H | H | NMR (400MHz, $CDCl_3$) δppm: 1.07(1H, m), 1.40(1H, m,), 1.71(3H, s), 1.74(3H, s), 2.09~2.14(1H, m), 3.39(1H, d, J=10.3Hz), 3.66(1H, dd, J=5.9Hz, 10.3Hz), 7.17~7.33(8H, m), 7.37~7.41(2H, m) IR $\nu$film($cm^{-1}$): 1683 |
| 4 | H | 3-F | H | H | NMR (400MHz, $CDCl_3$) δppm: 1.04(1H, m), 1.31(1H, m,), 1.64(3H, s), 1.67(3H, s), 2.05~2.10(1H, m), 3.33(1H, d, J=10.3Hz), 3.58~3.62(1H, m), 6.80~6.85(1H, m), 7.07~7.11(2H, m), 7.13~7.21(2H, m), 7.23~7.25(4H, m) IR $\nu$film ($cm^{-1}$): 1683 |
| 5 | H | 3-Cl | H | H | NMR (400MHz, $CDCl_3$) δppm: 1.10(1H, m), 1.38(1H, m,), 1.70(3H, s), 1.75(3H, s), 2.13~2.17(1H, m), 3.40(1H, d, J=10.3Hz), 3.67(1H, m), 7.17~7.43(9H, m) IR $\nu$film($cm^{-1}$): 1683 |
| 6 | H | 3-F | H | $CH_3$ | NMR (400MHz, $CDCl_3$) δppm: 1.11(3H, s), 1.13(1H, d, J=4.8Hz), 1.37(1H, d, J=4.8Hz), 1.73(3H, s), 1.77(3H, s), 3.36(1H, d, J=10.3Hz), 3.46(1H, d, J=10.3Hz), 6.88~6.97(3H, m), 7.18~7.54(6H, m) IR $\nu$KBr($cm^{-1}$): 1677 m.p. 138.5~141.0° C. |
| 7 | 3-Cl | 2-Cl | H | $CH_3$ | NMR (400MHz, $CDCl_3$) δppm: |

TABLE 1-continued

| Compound No. | Substituents in formula (1) | | | | Physical properties |
|---|---|---|---|---|---|
| | Xm | Yn | R₁ | R₂ | |
| | | | | | 1.13(3H, s), 1.20(1H, d, J=5.1Hz), 1.29(1H, d, J=5.1Hz), 1.66(3H, s), 1.73(3H, s), 3.57(1H, d, J=10.3Hz), 3.62(1H, d, J=10.3Hz), 7.16~7.29(6H, m), 7.32~7.38(2H, m) IR νKBr(cm⁻¹): 1671 m.p. 150.5~152.5° C. |
| 8 | 3-Cl | 3-Cl | H | CH₃ | NMR (400MHz, CDCl₃) δppm: 1.12(3H, s), 1.14(1H, d, J=5.1Hz), 1.39(1H, d, J=5.1Hz), 1.67(3H, s), 1.73(3H, s), 3.42(1H, d, J=10.3Hz), 3.55(1H, d, J=10.3Hz), 7.07~7.10(1H, m), 7.17~7.28(7H, m) IR νfilm(cm⁻¹): 1687 |
| 9 | 3-Cl | 4-Cl | H | CH₃ | NMR (400MHz, CDCl₃) δppm: 1.10(3H, s), 1.13(1H, d, J=4.4Hz), 1.37(1H, d, J=4.4Hz), 1.66(3H, s), 1.72(3H, s), 3.42(1H, d, J=10.3Hz), 3.56(1H, d, J=10.3Hz), 7.13(2H, d, J=8.1Hz), 7.16~7.30(6H, m) IR νfilm(cm⁻¹): 1683 |
| 10 | 3-Cl | H | H | CH₃ | NMR (400MHz, CDCl₃) δppm: 1.11(3H, s), 1.12(1H, d, J=5.1Hz), 1.41(1H, d, J=5.1Hz), 1.67(3H, s), 1.73(3H, s), 3.42(1H, d, J=10.3Hz), 3.55(1H, d, J=10.3Hz), 7.16~7.33(9H, m) IR νfilm(cm⁻¹): 1686 |
| 11 | H | H | CH₃ | H | IR νfilm(cm⁻¹): 1686 n_D 23.6° C.: 1.5619 |
| 12 | H | 2-Cl | H | H | NMR (400MHz, CDCl₃) δppm: 1.12(1H, m), 1.47(1H, m,), 1.71(3H, s), 1.75(3H, s), 1.93~1.98(1H, m), 3.46(1H, d, J=10.3Hz), 3.79(1H, m), 7.17~7.37(9H, m) IR νfilm (cm⁻¹): 1672 |
| 13 | 3-Cl | 3-F | H | CH₃ | NMR (400MHz, CDCl₃) δppm: 1.12(3H, s), 1.14(1H, d, J=5.1Hz), 1.39(1H, d, J=5.1Hz), 1.67(3H, s), 1.73(3H, s), 3.42(1H, d, J=10.3Hz), 3.55(1H, d, J=10.3Hz), 6.88~6.99(3H, m), 7.13~7.28(5H, m) IR νfilm(cm⁻¹): 1687 |
| 14 | 3-CH₃ | 2-F | H | CH₃ | NMR (400MHz, CDCl₃) δppm: 1.08(3H, s), 1.17(1H, d, J=5.1Hz), 1.28(1H, d, J=5.1Hz), 1.72(6H, s), 2.34(3H, s), 3.43(1H, d, J=10.3Hz), 3.53(1H, d, J=10.3Hz), 7.00~7.30(8H, m) m.p. 94.0~96.0° C. IR νKBr(cm⁻¹): 1672 |
| 15 | 4-Cl | 2-F | H | CH₃ | NMR (400MHz, CDCl₃) δppm: 1.07(3H, s), 1.16(1H, d, J=5.1Hz), 1.31(1H, d, J=5.1Hz), 1.68(3H, s), 1.69(3H, s), 3.49(1H, d, J=10.4Hz), 3.60(1H, d, J=10.4Hz), 7.00~7.10(2H, m), 7.18~7.31(6H, m) IR νnujol(cm⁻¹) m.p. 109.0~112.0° C. |
| 16 | 3-F | 2-F | H | CH₃ | NMR (400MHz, CDCl₃) δppm: 1.10(3H, s), 1.19(1H, d, J=5.1Hz), 1.32(1H, d, J=5.1Hz), 1.68(3H, s), 1.70(3H, s), 3.50(1H, d, J=10.3Hz), 3.60(1H, d, J=10.3Hz), 6.86~6.91(1H, m), 7.01~7.12(4H, m), 7.19~7.30(3H, m) IR νKBr(cm⁻¹): 1686 m.p. 108.0~111.0° C. |
| 17 | 3-Cl | 2-F | H | H | NMR (400MHz, CDCl₃) δppm: 1.08(1H, m), 1.51(1H, m,), 1.66(3H, s), 1.68(3H, s), 2.02~2.06(1H, m), 3.52(1H, d, J=9.5Hz), 3.79~3.83(1H, m), 6.98~7.08(2H, m), 7.16~7.34(6H, m) IR νfilm(cm⁻¹): 1690 |
| 18 | 3-Cl | H | H | H | NMR (400MHz, CDCl₃) δppm: 1.07(1H, m), 1.43(1H, m,), 1.65(3H, s), 1.70(3H, s), 2.10~2.20(1H, m), 3.48(1H, d, J=10.3Hz), 3.73(1H, dd, J=5.9Hz, 10.3Hz), 7.13~7.31(7H, m), 7.36~7.41(2H, m) IR νfilm(cm⁻¹): 1686 |
| 20 | 3-Cl | 3-CH₃ | H | CH₃ | IR νKBr(cm⁻¹): 1680 m.p. 110.0~111.0° C. |
| 19 | 3-F | H | H | CH₃ | NMR (400MHz, CDCl₃) δppm: 1.10(3H, s), 1.12(1H, d, J=5.4Hz), 1.40(1H, d, J=5.4Hz), 1.68(3H, s), 1.73(3H, s), 3.42(1H, d, J=10.3Hz), 3.54(1H, d, J=10.3Hz), 6.87~6.92(1H, m), 6.99~7.04(1H, m), 7.10(1H, d, J=8.1Hz), 7.18~7.35(6H, m) IR νKBr(cm⁻¹): 1680 m.p. 121.0~123.0° C. |
| 21 | 3-Cl | 4-F | H | CH₃ | NMR (400MHz, CDCl₃) δppm: 1.12(3H, s), 1.13(1H, d, J=4.4Hz), 1.35(1H, d, J=4.4Hz), 1.67(3H, s), 1.72(3H, s), 3.42(1H, d, J=10.3Hz), 3.56(1H, d, J=10.3Hz), 6.99(2H, t, J=8.4Hz), 7.14~7.28(6H, m) IR νfilm(cm⁻¹): 1686 |
| 22 | 3-Cl | 2,4-F₂ | H | CH₃ | NMR (400MHz, CDCl₃) δppm: 1.11(3H, s), 1.19(1H, d, J=4.8Hz), 1.28(1H, d, J=4.8Hz), 1.66(3H, s), 1.68(3H, s), 3.50(1H, d, J=9.5Hz), 3.60(1H, d, J=9.5Hz), 6.77~6.83(2H, m), 7.16~7.29(5H, m) IR νKBr(cm⁻¹): 1680 m.p. 106.0~109.0° C. |
| 23 | 3-Cl | 3,5-F₂ | H | CH₃ | NMR (400MHz, CDCl₃) δppm: 1.14(3H, s), 1.16(1H, d, J=5.1Hz), 1.38(1H, d, J=5.1Hz), 1.67(3H, s), 1.73(3H, s), 3.42(1H, d, J=10.3Hz), 3.55(1H, d, J=10.3Hz), |

TABLE 1-continued

| Compound No. | Substituents in formula (1) | | | | Physical properties |
|---|---|---|---|---|---|
| | Xm | Yn | R₁ | R₂ | |
| 24 | 3-iso-C₃H₇ | 2-F | H | CH₃ | 6.69~6.75(3H, m), 7.18~7.28(4H, m)<br>IR νfilm(cm⁻¹): 1687<br>NMR (400MHz, CDCl₃) δppm:<br>1.07(3H, s), 1.17(1H, d, J=4.4Hz), 1.25(6H, d, J=6.6Hz),<br>1.28(1H, d, J=4.4Hz), 1.74(6H, s), 2.90(1H, septet, J=6.6Hz),<br>3.42(1H, d, J=10.3Hz), 3.48(1H, d, J=10.3Hz), 7.00~7.28(8H, m) |
| 25 | 3-iso-C₃H₇ | H | H | CH₃ | IR νfilm(cm⁻¹): 1691<br>NMR (400MHz, CDCl₃) δppm:<br>1.07(3H, s), 1.11(1H, d, J=4.4Hz), 1.25(6H, d, J=6.6Hz),<br>1.36(1H, d, J=4.4Hz), 1.75(3H, s), 1.77(3H, s), 2.90(1H, septet, J=6.6Hz),<br>3.34(1H, d, J=10.3Hz), 3.43(1H, d, J=10.3Hz), 7.06~7.39(9H, m) |
| 26 | 3,5-Cl₂ | 2-F | H | H | IR νfilm(cm⁻¹): 1683<br>NMR (400MHz, CDCl₃) δppm:<br>1.08(1H, m), 1.55(1H, m,), 1.63(3H, s), 1.65(3H, s), 2.07~2.09(1H, m),<br>3.60(1H, m), 3.87(1H, m), 6.96~7.09(2H, m), 7.18(3H, m),<br>7.22~7.31(2H, m)<br>IR νKBr(cm⁻¹): 1688<br>m.p. 98.0~101.0 °C. |
| 27 | 3,5-Cl₂ | H | H | H | NMR (400MHz, CDCl₃) δppm:<br>1.08(1H, m), 1.49(1H, m,), 1.61(3H, s), 1.67(3H, s), 2.20~2.22(1H, m),<br>3.55(1H, m), 3.80(1H, m), 7.15~7.19(2H, m), 7.21~7.31(4H, m),<br>7.34~7.38(2H, m)<br>IR νfilm(cm⁻¹): 1684 |
| 28 | 3,5-Cl₂ | H | H | CH₃ | NMR (400MHz, CDCl₃) δppm:<br>1.12(1H, m), 1.14(3H, s), 1.43(1H, m), 1.65(3H, s), 1.70(3H, s),<br>3.48(1H, d, J=9.5Hz), 3.63(1H, d, J=9.5Hz), 7.13~7.22(5H, m),<br>7.24~7.32(3H, m)<br>IR νKBr(cm⁻¹): 1678<br>m.p. 124.3~126.3° C. |
| 29 | 3,5-Cl₂ | 2-F | H | CH₃ | NMR (400MHz, CDCl₃) δppm:<br>1.13(3H, s), 1.19(1H, m), 1.35(1H, m), 1.63(3H, s), 1.66(3H, s),<br>3.56(1H, d, J=9.5Hz), 3.67(1H, d, J=9.5Hz), 7.00~7.09(2H, m),<br>7.19~7.28(5H, m)<br>IR νfilm(cm⁻¹): 1684 |
| 30 | 3-Cl | 2,6-F₂ | H | CH₃ | NMR (400MHz, CDCl₃) δppm:<br>1.18(3H, s), 1.37(1H, d, J=4.4Hz), 1.41~1.43(1H, m), 1.68(6H, s),<br>3.49(1H, d, J=10.3Hz), 3.60(1H, d, J=10.3Hz), 6.82~6.91(2H, m),<br>7.14~7.30(5H, m)<br>IR νKBr(cm⁻¹): 1684<br>m.p. 113~115° C. |
| 31 | 3-CF₃ | 2-F | H | CH₃ | NMR (400MHz, CDCl₃) δppm:<br>1.12(3H, s)1.19(1H, d, J=4.4Hz), 1.34(1H, d, J=4.4Hz), 1.69(3H, s),<br>1.72(3H, s), 3.57(1H, d, J=9.5Hz), 3.67(1H, d, J=9.5Hz), 6.98~7.12(2H, m)<br>7.17~7.29(2H, m), 7.38~7.49(2H, m), 7.51~7.59(2H, m)<br>IR νKBr(cm⁻¹): 1671<br>m.p. 109.0~112.0° C. |
| 32 | 3-CF₃ | H | H | CH₃ | NMR (400MHz, CDCl₃) δppm:<br>1.09~1.15(4H, m), 1.42(1H, d, J=4.4Hz), 1.68(3H, s), 1.75(3H, s),<br>3.48(1H, d, J=10.3Hz), 3.63(1H, d, J=10.3Hz), 7.13~7.33(5H, m),<br>7.40~7.57(4H, m)<br>IR νfilm(cm⁻¹): 1684 |
| 33 | 3-OCH₃ | 2-F | H | CH₃ | NMR (400MHz, CDCl₃) δppm:<br>1.06(3H, s), 1.15(1H, d, J=4.4Hz), 1.26(1H, d, J=4.4Hz), 1.72(6H, s),<br>3.40(1H, d, J=10.3Hz), 3.47(1H, d, J=10.3Hz), 3.79(3H, s)<br>6.83~6.89(2H, m), 6.99~7.11(2H, m), 7.19~7.29(4H, m)<br>IR νfilm(cm⁻¹): 1690 |
| 34 | 3-Br | 2-F | H | CH₃ | IR νKBr(cm⁻¹): 1671<br>m.p. 130.3~131.2° C. |
| 35 | 3,4-Cl₂ | 2-F | H | CH₃ | NMR (400MHz, CDCl₃) δppm:<br>1.12(3H, 1s), 1.17(1H, d, J=5.1Hz), 1.34(1H, d, J=5.1Hz), 1.65(3H, s),<br>1.67(3H, s), 3.55(1H, d, J=10.2Hz), 3.66(1H, d, J=10.2Hz),<br>6.96~7.29(5H, m), 7.35~7.39(2H, m)<br>IR νKBr(cm⁻¹): 1670<br>m.p. 161.8~163.6° C. |
| 36 | 3,4-Cl₂ | H | H | CH₃ | NMR (400MHz, CDCl₃) δppm:<br>1.11(1H, d, J=4.4Hz), 1.13(3H, s), 1.42(1H, d, J=4.4Hz), 1.64(3H, s),<br>1.71(3H, s), 3.46(1H, d, J=10.3Hz), 3.62(1H, d, J=10.3Hz),<br>7.15~7.38(8H, m)<br>IR νfilmcm⁻¹: 1683 |
| 37 | 3-Br | H | H | CH₃ | NMR (400MHz, CDCl₃) δppm:<br>1.11(3H, s), 1.12(1H, d, J=5.1Hz), 1.41(1H, d, J=5.1Hz), 1.67(3H, s),<br>1.73(3H, s), 3.43(1H, d, J=10.3Hz), 3.57(1H, d, J=10.3Hz),<br>7.15~7.35(8H, m), 7.43~7.45(1H, m)<br>IR νfilm(cm⁻¹): 1683 |
| 38 | 3-OCH₃ | H | H | CH₃ | NMR (400MHz, CDCl₃) δppm:<br>1.07(3H, s), 1.11(1H, d, J=4.4Hz), 1.37(1H, d, J=4.4Hz), 1.71(3H, s),<br>1.75(3H, s), 3.36(1H, d, J=10.3Hz), 3.47(1H, d, J=10.3Hz), 3.79(3H, s),<br>6.73~6.77(1H, m), 6.82~6.95(2H, m), 7.19~7.33(6H, m)<br>IR νfilm(cm⁻¹): 1687 |
| 39 | 3-OCH₃ | 2-F | H | CH₃ | IR νKBr(cm⁻¹): 1680 |

TABLE 1-continued

| Compound No. | Substituents in formula (1) | | | | Physical properties |
|---|---|---|---|---|---|
| | Xm | Yn | $R_1$ | $R_2$ | |
| 40 | 3,4,5-Cl$_3$ | 2-F | H | CH$_3$ | m.p. 106.0~108.1° C.<br>NMR (400MHz, CDCl$_3$) δppm:<br>1.14(3H, s), 1.17(1H, d, J=4.4Hz), 1.37(1H, d, J=4.4Hz), 1.61(3H, s),<br>1.64(3H, s), 3.58(1H, d, J=9.5Hz), 3.70(1H, d, J=9.5Hz), 7.00~7.34(6H, m)<br>IR νfilm(cm$^{-1}$): 1672 |
| 41 | 3,4,5-Cl$_3$ | H | H | CH$_3$ | NMR (400MHz, CDCl$_3$) δppm:<br>1.11(1H, d, J=4.4Hz), 1.15(3H, s), 1.45(1H, d, J=4.4Hz), 1.61(3H, s),<br>1.69(3H, s), 3.50(1H, d, J=10.3Hz), 3.67(1H, d, J=10.3Hz)<br>7.16~7.33(7H, m)<br>IR νfilm(cm$^{-1}$): 1682 |
| 42 | 3,5-Cl$_2$-4-OCH$_3$ | 2-F | H | CH$_3$ | NMR (400MHz, CDCl$_3$) δppm: 1.14(3H, s)<br>1.17(1H, d, J=4.4Hz), 1.37(1H, d, J=<br>4.4Hz), 1.61(3H, s), 1.64(3H, s), 3.59<br>(1H, d, J=9.5Hz), 3.72(1H, d, J=9.5Hz),<br>3.85(3H, s), 7.00~7.50(6H, m)<br>IR νfilm(cm$^{-1}$): 1674 |
| 43 | 3,5-Cl$_2$-4-OCH$_3$ | H | H | CH$_3$ | NMR (400MHz, CDCl$_3$) δppm:<br>1.12(1H, d, J=4.4Hz), 1.16(3H, s), 1.45(1H, d, J=4.4Hz), 1.63(3H, s),<br>1.69(3H, s), 3.52(1H, d, J=10.3Hz), 3.68(1H, d, J=10.3Hz), 3.85(3H, s),<br>7.05~7.45(7H, m)<br>IR νfilm(cm$^{-1}$): 1685 |
| 44 | 3-Cl 5-F | 2-F | H | CH$_3$ | NMR (400MHz, CDCl$_3$) δppm:<br>1.15(3H, s), 1.16(1H, d, J=5.1Hz), 1.36(1H, d, J=5.1Hz), 1.62(3H, s),<br>1.65(3H, s), 3.58(1H, d, J=9.3Hz), 3.70(1H, d, J=9.3Hz), 7.91~7.40(7H, m)<br>IR νfilmcm$^{-1}$: 1673 |
| 45 | 3-Cl 5-F | H | H | CH$_3$ | NMR (400MHz, CDCl$_3$) δppm:<br>1.11(1H, d, J=4.4Hz), 1.15(3H, s), 1.45(1H, d, J=4.4Hz), 1.61(3H, s),<br>1.69(3H, s), 3.50(1H, d, J=10.3Hz), 3.67(1H, d, J=10.3Hz),<br>7.16~7.33(8H, m)<br>IR νfilm(cm$^{-1}$): 1684 |

Preparation examples of intermediates will be described as reference examples.

Reference Example 1

Preparation of 1-[1-methyl-1-(3-chlorophenyl)ethyl]-4-bromomethyl-4-methyl-3-(2-fluorophenyl)pyrrolidine-2-one To 20 ml of toluene were added 2.0 g of N-[1-methyl-1-(3-chlorophenyl)ethyl]-N-(2-methyl-2-propenyl)-2-bromo-2-(2-fluorophenyl)acetamide, 0.5 g of cuprous chloride and 0.6 g of di-n-butylamine, and the solution was then stirred at a reflux temperature for 0.5 hour. After cooling, the reaction solution was poured into water, and extraction was made with toluene. The resultant extract was dried over anhydrous sodium sulfate, and concentration, silica gel column chromatography was done to obtain 0.8 g of the desired 1-[1-methyl-1-(3-chlorophenyl)ethyl]-4-bromomethyl--4-methyl-3-(2-fluorophenyl)pyrrolidine-2-one.

Reference Example 2

Preparation of 1-(1-methyl-1-phenylethyl)-4-bromomethyl-3-(3-fluorophenyl)pyrrolidine-2-one To 15 ml of benzene were added 1.2 g of N-(1-methyl-1-phenylethyl)-N-(2-propenyl)-2-bromo-2-(3-fluorophenyl)acetamide, 0.2 g of cuprous chloride and 0.3 g of di-n-butylamine, and the solution was then stirred at a reflux temperature for 1 hour. After cooling, the reaction solution was poured into water, and extraction was made with benzene. The resultant extract was dried over anhydrous sodium sulfate, and after concentration, silica gel column chromatography was done to obtain 0.9 g of the desired 1-(1-methyl-1-phenylethyl)-4-bromomethyl-3-(3-fluorophenyl)pyrrolidine-2-one.

Other pyrrolidinone derivatives represented by the formula (II) were synthesized by the same procedures as in Reference Example 1 or 2. Physical properties of the synthesized derivatives are shown in Table 2.

TABLE 2

| Substituents in formula (II) | | | | | Physical properties |
|---|---|---|---|---|---|
| Xm | Yn | $Z_1$ | $R_1$ | $R_2$ | |
| 3-Cl | 2-F | Br | H | CH$_3$ | NMR(400MHz, CDCl$_3$)δppm:<br>1.78(3H, s), 1.79(3H, s), 2.17(3H, s)3.20~3.70(4H, m), 3.90~4.00(1H, M),<br>7.00~7.18(3H, m), 7.20~7.30(4H, m), 7.37(1H, s)<br>IR νfilm(cm$^{-1}$): 1694 |
| H | 3-F | Br | H | H | NMR(400MHz, CDCl$_3$)δppm:<br>1.80(3H, s), 1.83(3H, s), 2.65~2.75(1H, m), 3.25~3.45(2H, m),<br>3.50~3.70(3H, m), 6.82~6.97(3H, m), 7.20~7.45(6H, m)<br>IR νfilm(cm$^{-1}$): 1690 |
| H | H | Cl | H | H | NMR(400MHz, CDCl$_3$)δppm:<br>1.80(3H, s), 1.83(3H, s), 2.65~2.74(1H, m), 3.32(1H, dd, J=7.3Hz, 9.5Hz),<br>3.48~3.66(4H, m), 7.15~7.44(10H, m)<br>IR νfilm(cm$^{-1}$): 1695 |
| H | 3-F | Br | H | CH$_3$ | IR νfilm(cm$^{-1}$): 1694<br>n$_D$ 24.6° C.: 1.5462 |
| H | 2-Cl | Br | H | H | IR νfilm(cm$^{-1}$): 1694<br>n$_D$ 25.8° C.: 1.5717 |
| H | H | Cl | CH$_3$ | H | NMR(400MHz, CDCl$_3$)δppm:<br>1.35~1.42(3H, m), 1.80(3H, s), 1.84(3H, s), 2.58~2.80(1H, m),<br>3.33~3.70(4H, m), 7.15~7.35(10H, m) |

TABLE 2-continued

| Substituents in formula (II) | | | | | |
|---|---|---|---|---|---|
| Xm | Yn | $Z_1$ | $R_1$ | $R_2$ | Physical properties |
| | | | | | IR $\nu$film(cm$^{-1}$): 1694 |
| 3-Cl | H | Cl | H | $CH_3$ | IR $\nu$film(cm$^{-1}$): 1695 oily |
| 3-Cl | 3-F | Br | H | $CH_3$ | IR $\nu$film(cm$^{-1}$): 1693 oily |
| H | 3-Cl | Br | H | H | NMR(400MHz, CDCl$_3$)$\delta$ppm: 1.80(3H, s), 1.83(3H, s), 2.60~2.75(1H, m), 3.25~3.46(2H, m), 3.48~3.68(3H, m), 7.06~7.43(9H, m) IR $\nu$film(cm$^{-1}$): 1690 |
| 3-Cl | 4-Cl | Br | H | $CH_3$ | IR $\nu$film(cm$^{-1}$): 1696 oily |
| 3-Cl | 2-Cl | Br | H | $CH_3$ | IR $\nu$film(cm$^{-1}$): 1696 oily |
| 3-Cl | 3-Cl | Br | H | $CH_3$ | IR $\nu$film(cm$^{-1}$): 1698 $n_D$ 22.8° C.: 1.5716 |
| H | H | Cl | H | $CH_3$ | IR $\nu$film(cm$^{-1}$): 1694 $n_D$ 20.4° C.: 1.5604 |
| 3-$CH_3$ | 2-F | Br | H | $CH_3$ | IR $\nu$film(cm$^{-1}$): 1698 $n_D$ 24.7° C.: 1.5419 |
| 4-Cl | 2-F | Br | H | $CH_3$ | IR $\nu$film(cm$^{-1}$): 1695 $n_D$ 23.7° C.: 1.5525 |
| 3-Cl | 2-F | Br | H | H | IR $\nu$film(cm$^{-1}$): 1698 $n_D$ 25.3° C.: 1.5697 |
| 3-F | 2-F | Br | H | $CH_3$ | IR $\nu$film(cm$^{-1}$): 1698 $n_D$ 24.1° C.: 1.5453 |
| 3-Cl | H | Cl | H | H | IR $\nu$film(cm$^{-1}$): 1695 $n_D$ 25.3° C.: 1.5605 |
| 3-F | H | Cl | H | $CH_3$ | IR $\nu$film(cm$^{-1}$): 1696 $n_D$ 28.9° C.: 1.5494 |
| 3-Cl | 4-F | Br | H | $CH_3$ | IR $\nu$film(cm$^{-1}$): 1695 $n_D$ 23.4° C.: 1.5532 |
| 3-Cl | 2-$CH_3$ | Cl | H | $CH_3$ | IR $\nu$film(cm$^{-1}$): 1694 $n_D$ 23.5° C.: 1.5602 |
| 3-Cl | 2,4-$F_2$ | Br | H | $CH_3$ | IR $\nu$film(cm$^{-1}$1): 1695 $n_D$ 23.5° C.: 1.5555 |
| 3-Cl | 3,5-$F_2$ | Br | H | $CH_3$ | IR $\nu$film(cm$^{-1}$): 1695 $n_D$ 22.4° C.: 1.5613 |
| 3-iso-$C_3H_7$ | 2-F | Br | H | $CH_3$ | IR $\nu$film(cm$^{-1}$): 1698 $n_D$ 21.9° C.: 1.5426 |
| 3-iso-$C_3H_7$ | H | Cl | H | $CH_3$ | IR $\nu$film(cm$^{-1}$): 1695 $n_D$ 22.3° C.: 1.5446 |
| 3-Cl | 2,6-$F_2$ | Br | H | $CH_3$ | IR $\nu$film(cm$^{-1}$): 1696 oily |

Reference Example 3

Preparation of N-[1-methyl-1-(3-chlorophenyl)ethyl]-N-(2-methyl-2-propenyl)-2-bromo-2-(2-fluorophenyl)acetamide In 30 ml of dichloromethane containing 2.8 g of pyridine, 4.0 g of 2-bromo-2-(2-fluorophenyl)acetyl chloride were added dropwise to 2.5 g of N-[1-methyl-1-(3-chlorophenyl)ethyl]-2-methyl-2-propenylamine at 10° to 15° C. After stirring at room temperature for 1 hour, the solution was poured into water, and extraction was then made with dichloromethane. The resultant extract was washed with a saturated aqueous sodium bicarbonate solution, and dried over anhydrous sodium sulfate. After concentration, column chromatography was done to obtain 2.0 g of the desired N-[1-methyl-1-(3-chlorophenyl)ethyl]-N-(2-methyl-2-propenyl)-2-bromo-2-(2-fluorophenyl)acetamide.

Reference Example 4

Preparation of N-[1-methyl-1-(3,5-dichlorophenyl)ethyl]-N-(2-propenyl)-2-chloro-2-phenylacetamide In 15 ml of dichloromethane containing 1.3 g of pyridine and 0.53 g of N-ethyldiisopropylamine, 2 ml of a dichloromethane solution containing 0.93 g of 2-chloro-2-phenylacetyl chloride were added dropwise to 1.0 g of N-[1-methyl-1-(3,5-dichlorophenyl)ethyl]-2-propenylamine at ice subzero temperature. Afterward, the solution was stirred at room temperature for 1 hour, and then poured into water, followed by extraction with ethyl acetate. The resultant extract was washed with a saturated aqueous sodium bicarbonate solution, and then dried over anhydrous magnesium sulfate. After concentration, column chromatography was done to obtain 1.2 g of the desired N-[1-methyl-1-(3,5-dichlorophenyl)ethyl]-N-(2-propenyl)-2-chloro-2-phenylacetamide.

Other acetamide derivatives represented by the formula (III) were synthesized by the same procedures as in Reference Example 3 or 4. Physical properties of the synthesized derivatives are shown in Table 3.

TABLE 3

| Substituents in formula (III) | | | | | |
|---|---|---|---|---|---|
| Xm | Yn | $Z_1$ | $R_1$ | $R_2$ | Physical properties |
| 3-Cl | 2-F | Br | H | $CH_3$ | NMR(400MHz, CDCl$_3$)$\delta$ppm: 1.50(6H, s), 1.82(3H, s), 3.90~4.20(2H, m), 5.08~5.15(2H, m), |

TABLE 3-continued

| Substituents in formula (III) | | | | | |
|---|---|---|---|---|---|
| Xm | Yn | $Z_1$ | $R_1$ | $R_2$ | Physical properties |
|  |  |  |  |  | 5.85~5.95(1H, m), 7.10~7.45(8H, m)<br>IR νfilm(cm$^{-1}$): 1676 |
| H | 3-F | Br | H | CH$_3$ | IR νfilm(cm$^{-1}$): 1674<br>n$_D$ 25.6° C.: 1.5462 |
| H | H | Cl | H | H | IR νfilm(cm$^{-1}$): 1673<br>n$_D$ 22.1° C.: 1.5713 |
| 3-Cl | H | Cl | H | CH$_3$ | IR νfilm(cm$^{-1}$): 1676<br>oily |
| 3-Cl | 3-F | Br | H | CH$_3$ | IR νfilm(cm$^{-1}$): 1673<br>oily |
| H | 2-Cl | Br | H | H | NMR(400MHz, CDCl$_3$)δppm:<br>1.64(6H, s), 4.15~4.30(2H, m), 5.25~5.45(3H, m), 5.95~6.20(1H, m), 7.15~7.62(9H, m)<br>IR νfilm(cm$^{-1}$): 1669 |
| H | H | Cl | CH | H | NMR(400MHz, CDCl$_3$)δppm:<br>1.65(6H, s), 1, 85(3H, s), 4.00~4.18(2H, m), 5.42~5.78(3H, m), 7.15~7.58(10H, m)<br>IR νfilm(cm$^{-1}$): 1674 |
| H | 3-Cl | Br | H | H | NMR(400MHz, CDCl$_3$)δppm:<br>1.71(6H, s), 4.05~4.30(2H, m), 5.32~5.43(2H, m), 5.45~5.60(1H, m), 5.95~6.10(1H, m), 7.15~7.50(9H, m)<br>IR νfilm(cm$^{-1}$): 1670 |
| H | 3-F | Br | H | H | NMR(400MHz, CDCl$_3$)δppm:<br>1.58(6H, s), 4.05~4.25(2H, m), 5.35~5.40(2H, m), 5.50~5.60(1H, m), 5.95~6.05(1H, m), 7.90~7.40(9H, m)<br>IR νfilm(cm$^{-1}$): 1671 |
| 3-Cl | 3-Cl | Br | H | CH$_3$ | NMR (60MHz, CDCl$_3$)δppm:<br>1.50(6H, s), 1.83(3H, s), 4.07~4.20(1H, m), 4.75~5.25(3H, m), 5.45~5.55(1H, m), 7.10~7.45(8H, m)<br>IR νfilm(cm$^{-1}$): 1674 |
| 3-Cl | 2-Cl | Br | H | CH$_3$ | NMR(400MHz, CDCl$_3$)δppm:<br>1.48(6H, s), 1.87(3H, s), 3.75~4.20(2H, m), 5.12~5.20(2H, m), 6, 15(1H, s), 7.02~7.48(8H, m)<br>IR νKBr(cm$^{-1}$): 1668<br>m.p. 117.0~120° C. |
| 3-Cl | 4-Cl | Br | H | CH$_3$ | IR νfilm (cm$^{-1}$): 1679<br>oily |
| H | H | Cl | H | CH$_3$ | NMR(600MHz, CDCl$_3$)δppm:<br>1.63~1.97(9H, m), 3.97~4.30(2H, m), 4.95~5.33(2H, m), 5.50~5.55(1H, m), 7.07~7.45(10H, m)<br>IR νfilm(cm$^{-1}$): 1676 |
| 3-F | H | Br | F | CH$_3$ | IR νfilm(cm$^{-1}$): 1674<br>n$_D$ 24.0° C.: 1.5527 |
| 3-Cl | 2-F | Br | H | H | IR νfilm(cm$^{-1}$): 1671<br>n$_D$ 22.9° C.: 1.5693 |
| 3-CH$_3$ | 2-F | Br | H | CH$_3$ | IR νfilm(cm$^{-1}$): 1676<br>n$_D$ 22.9° C.: 1.5806 |
| 4-Cl | 2-F | Br | H | CH$_3$ | IR νKBr(cm$^{-1}$): 1669<br>m.p. 105.0~107.0° C. |
| 3-Cl | H | Cl | H | H | IR νfilm(cm$^{-1}$): 1673<br>n$_D$ 22.9° C.: 1.5717 |
| 3-Cl | 2-CH$_3$ | Cl | H | CH$_3$ | IR νfilm(cm$^{-1}$): 1679<br>n$_D$ 23.1° C.: 1.5668 |
| 3-F | H | Cl | H | CH$_3$ | IR νfilm(cm$^{-1}$): 1676<br>n$_D$ 21.7° C.: 1.5586 |
| 3-Cl | 4-F | Br | H | CH$_3$ | IR νfilm(cm$^{-1}$): 1674<br>n$_D$ 22.8° C.: 1.5434 |
| 3-Cl | 2,4-F$_2$ | Br | H | CH$_3$ | IR νfilm(cm$^{-1}$): 1675<br>n$_D$ 24.3° C.: 1.5423 |
| 3-Cl | 3,5-F$_2$ | Br | H | CH$_3$ | IR νfilm(cm$^{-1}$): 1674<br>n$_D$ 20.7° C.: 1.5529 |
| 3-iso-C$_3$H$_7$ | H | Cl | H | CH$_3$ | IR νfilm(cm$^{-1}$): 1679<br>n$_D$ 23.1° C.: 1.5510 |
| 3-iso-C$_3$H$_7$ | 2-F | Br | H | CH$_3$ | IR νfilm(cm$^{-1}$): 1675<br>n$_D$ 19.7° C.: 1.5502 |
| 3,5-Cl$_2$ | H | Cl | H | H | NMR(400MHz, CDCl$_3$)δppm:<br>1.54(3H, s), 1.74(3H, s), 4.11~4.25(2H, m), 5.35~5.45(2H, m), 5.60(1H, s), 5.95(1H, m), 7.03(2H, m), 7.18(1H, m), 7.28~7.40(5H, m)<br>IR νfilm(cm$^{-1}$): 1671 |
| 3-Cl | 2,6-F$_2$ | Br | H | CH$_3$ | IR νKBr (cm$^{-1}$): 1682<br>m.p. 117.0~120.0° C. |
| 3,5-Cl$_2$ | 2-F | Br | H | H | NMR(400MHz, CDCl$_3$)δppm:<br>1.60(3H, s), 1.70(3H, s), 4.08~4.14(1H, m), 4.30~4.36(1H, m), 5.35~5.45(2H, m), 5.96(1H, s), 6.01(1H, m)7.02~7.06(3H, m), 7.16~7.18(2H, m), 7.30(1H, m), 7.52(1H, m)<br>IR νfilm(cm$^{-1}$): 1671 |
| 3,5-Cl$_2$ | H | Cl | H | CH$_3$ | NMR(400MHz, CDCl$_3$)δppm:<br>1.54(3H, s), 1.76(3H, s), 1.83(3H, s), 4.11(2H, m), 5.11(1H, s), 5.19(1H, m), 5.51(1H, s), 7.04(2H, m), 7.15~7.37(6H, m)<br>IR νfilm(cm$^{-1}$): 1675 |

TABLE 3-continued

| Substituents in formula (III) | | | | | |
|---|---|---|---|---|---|
| Xm | Yn | $Z_1$ | $R_1$ | $R_2$ | Physical properties |
| 3,5-Cl$_2$ | 2-F | Br | H | CH$_3$ | NMR(400MHz, CDCl$_3$)δppm: 1.57(3H, s), 1.74(3H, s), 1.84(3H, s), 4.13(2H, m), 5.09(1H, s), 5.16(1H, m), 5.94(1H, s), 7.04(2fl, m), 7.14~7.21(2H, m), 7.26~7.36(2H, m), 7.51(1H, m) IR νfilm(cm$^{-1}$): 1675 |
| 3-Cl | 2,6-F$_2$ | Br | H | CH$_3$ | IR νKBr(cm$^{-1}$): 1682 m.p. 117.0~120.0° C. |
| 3-CF$_3$ | 2-F | Br | H | CH$_3$ | IR νfilm(cm$^{-1}$): 1673 n$_D$ 22.5° C.: 1.5193 |
| 3-CF$_3$ | H | Cl | H | CH$_3$ | IR νfilm(cm$^{-1}$): 1675 n$_D$ 22.5° C.: 1.5328 |
| 4-OCH$_3$ | 2-F | Br | H | CH$_3$ | IR νfilm(cm$^{-1}$): 1672 n$_D$ 21.7° C.~1.5519 |
| 3,4-Cl$_2$ | 2-F | Br | H | CH$_3$ | IR νKBr(cm$^{-1}$): 1664 m.p. 117.0~119.0° C. |
| 3-Br | H | Cl | H | CH$_3$ | IR νfilm(cm$^{-1}$): 1676 n$_D$ 21.1° C.: 1.5669 |
| 3,4-Cl$_2$ | H | Cl | H | CH$_3$ | NMR(400MHz, CDCl$_3$)δppm: 1.58(3H, s), 1.74(3H, s), 1.83(3H, s), 4.02(1H, d, J=19.0Hz), 4.13(1H, d, J=19.0Hz), 5.12(1H, s), 5.19(1H, s)5.49(1H, s), 7.06(1H, dd, J=2.2Hz, 8.1HZ), 7.21~7.65(7H, m) IR νfilm(cm$^{-1}$): 1671 |
| 3-Br | 2-F | Br | H | CH$_3$ | IR νfilm(cm$^{-1}$): 1671 m.p. 122.5~124.2° C. |
| 3-OCH$_3$ | 2-F | Br | H | CH$_3$ | IR νfilm(cm$^{-1}$): 1669 m.p. 136.1~138.5° C. |
| 3-OCH$_3$ | H | Cl | H | CH$_3$ | IR νfilm(cm$^{-1}$): 1676 n$_D$ 19.7° C.: 1.5564 |

TABLE 4

| Substituents in formula (IV) | | | |
|---|---|---|---|
| Xn | $R_1$ | $R_2$ | Physical properties |
| 3-Cl | H | CH$_3$ | NMR(400MHz, CDCl$_3$)δppm: 1.44(6H, s), 1.73(3H, s), 2.85(2H, s), 4.87 (1H, m), 4.90(1H, m), 7.17~7.26(2H, m), 7.30~7.34(1H, m), 7.45(1H, m) IR νfilm(cm$^{-1}$): 3360 |
| H | H | H | NMR(400MHz, CDCl$_3$)δppm: 1.47(6H, s), 2.94~2.96(2H, m), 5.00~5.03(1H, m), 5.04~5.11(1H, m), 5.86~5.95(1H, m), 7.21~7.44(5H, m) IR νfilm(cm$^{-1}$): 3328 |
| H | H | CH$_3$ | NMR(400MHz, CDCl$_3$)δppm: 1.46(6H, s), 1.71(3H, s), 2.85(2H, s), 4.76(1H, m), 4.90(1H, m), 7.19~7.21 (1H, m), 7.29(2H, m), 7.45(2H, m) IR νfilm(cm$^{-1}$): 3329 |
| H | CH$_3$ | H | NMR(400MHz, CDCl$_3$)δppm: 1.46(6H, s), 1.64(3H, m), 2.87(2H, s), 5.45~5.60(2H, m), 7.18~7.27(1H, m), 7.32(2H, m), 7.42(2H, m) IR νfilm(cm$^{-1}$): 3330 |
| 3-Cl | H | H | NMR(60MHz, CDCl$_3$)δppm: 1.49(6H, s), 2.89~3.13(2H, m), 4.95~5.30(2H, m), 5.76~6.05(1H, m), 7.12~7.60(4H, m) IR νfilm(cm$^{-1}$): 3336 n$_D$ 24.9° C.: 1.5384 |
| 3-CH$_3$ | H | CH$_3$ | NMR(60MHz, CDCl$_3$)δppm: 1.48(6H, s), 1.74(3H, s), 2.34(3H, s), 2.85 (2H, s), 4.80(1H, m), 4.88(1H, m), 6.85~7.28(4H, m) IR νfilm(cm$^{-1}$): 3381 n$_D$ 21.1° C.: 1.5153 |
| 3-F | H | CH$_3$ | NMR(60MHz, CDCl$_3$)δppm: 1.47(6H, s), 1.72(3H, s), 2.83(2H, s), 4.78 (1H, m), 4.85(1H, m), 6.78~7.31(4H, m) IR νfilm(cm$^{-1}$): 3336 n$_D$ 22.7° C.: 1.4987 |
| 4-Cl | H | CH$_3$ | NMR(60MHz, CDCl$_3$)δppm: 1.48(6H, s), 1.72(3H, s), 2.83(2H, s), 4.75~5.02(2H, m), 7.27(2H, s), 7.34 (2H, s) IR νfilm(cm$^{-1}$): 3332 n$_D$ 21.7° C.: 1.5260 |
| 3-iso-C$_3$H$_7$ | H | CH$_3$ | NMR(400MHz, CDCl$_3$)δppm: 1.25(6H, d, J=6.6Hz), 1.47(6H, s), 1.73 (3H, s), 2.87(2H, s), 2.90(1H, septet, J=6.6Hz), 4.75(1H, s), 4.90(1H, s), 7.08~7.10(1H, m), 7.24~7.25(2H, m), 7.33(1H, s) IR νfilm(cm$^{-1}$): 3328 n$_D$ 24.2° C.: 1.5001 |
| 3,5-Cl$_2$ | H | H | NMR(400MHz, CDCl$_3$)δppm: 1.44(6H, s), 2.95(2H, d, J=5, 9Hz), 5.05 (1H, dd, J=10.3Hz, 1.5Hz), 5.16(1H, dd, J=17.6Hz, 1.5Hz), 5.88 (1H, m), 7.21(1H, m), 7.34(2H, m) IR νfilm(cm$^{-1}$): 3330 |
| 3,5-Cl$_2$ | H | H | NMR(400MHz, CDCl$_3$)δppm: 1.43(6H, s), 1.74(3H, s), 2.85(2H, s), 4.79 (1H, s), 4.92(1H, s), 7.21(1H, m), 7.36 (2H, m) IR νfilm(cm$^{-1}$): 3335 |
| 3-CF$_3$ | H | CH$_3$ | IR νfilm(cm$^{-1}$): 3335 n$_D$ 19.9° C.: 1.4673 |
| 3-OCH$_3$ | H | CH$_3$ | IR νfilm(cm$^{-1}$): 3329 n$_D$ 19.4° C.: 1.5174 |
| 3-Br | H | CH$_3$ | NMR(400MHz, CDCl$_3$)δppm 1.38(6H, s), 1.77(3H, s), 2.75~3.00 (2H, m), 4.70~4.95(2H, m), 7.20~7.45 (2H, m), 7.52~7.60(1H, m), 7.80~8.00 (1H, m) IR νfilm(cm$^{-1}$): 3285 |
| 3,4,5-Cl$_3$ | H | CH$_3$ | IR νfilm(cm$^{-1}$): 3337 n$_D$ 24.5° C.: 1.4215 |

Reference Example 5

Preparation of N-[1-methyl-1-(3-chlorophenyl)ethyl]-2-methyl-2-propenylamine

To 15 ml of N,N-dimethylformamide were added 2.6 g of 1-methyl-1-(3-chlorophenyl)ethylamine, 2.0 g of potassium carbonate and 2.1 g of 3-chloro-2-methylpropene, and the solution was then stirred at 85° C. for 1 hour. After potassium carbonate was removed by filtration, 100 ml of water were added, followed by extraction with toluene. The resultant extract was dried over anhydrous sodium sulfate, and then concentrated by an evaporator. Afterward, silica gel column chromatography was done to obtain 2.6 g of the desired amine.

Furthermore, amine derivatives represented by the formula (IV) were obtained by the same method as in Reference Example 5. The physical properties of the derivatives are shown in Table 4.

Reference Example 6

Preparation of 1-methyl-1-[3-(1-methylethyl)phenyl]ethylamine

First, 0.5 g of platinum oxide was added to a solution formed by dissolving 25.3 g of 1-methyl-1-[3-(1-methylethenyl)phenyl]ethylamine in 100 ml of ethyl alcohol, and a hydrogenation reaction was then carried out at a temperature of 15° to 35° C. for 7 hours under atmospheric pressure under a hydrogen gas stream. Afterward, reaction residues were removed by filtration, and the resultant filtrate was then concentrated to obtain 25.0 g of 1-methyl-1-[3-(1-methylethyl)phenyl]ethylamine.

(400 MHz, CDCl$_3$) δ ppm: 1.23 (6H, d, J=7.4 Hz), 1.48 (6H, S), 2.91 (1H, septet, J=7.4 Hz), 7.06–7.10 (1H, m), 7.22–7.32 (2H, m), 7.36 (1H, broad s) IR ν film (cm$^{-1}$): 3362, 3287

Reference Example 7

Preparation of 1-methyl-1-[3-(1-methylethenyl)-phenyl]ethylamine 13.6 g of 1-methyl-1-[3-(1-methylethenyl)phenyl]ethyl isocyanate were dissolved in 30 ml of isopropyl alcohol, and 19.0 g of potassium hydroxide were then added to the solution, followed by stirring for 3 hours under heating and reflux. Afterward, the solution was concentrated under reduced pressure, and then poured into ice water. After extraction with dichloromethane, the resultant extract was dried over anhydrous magnesium sulfate. The solution was concentrated under reduced pressure again to obtain 10.5 g of 1-methyl-1-[3-(1-methylethenyl)phenyl]ethylamine.

NMR (400 MHz, CDCl$_3$) δ ppm: 1.51 (6H, S), 2.17 (3H, S), 5.09 (1H, S), 5.37 (1H, S), 7.28–7.33 (2H, m), 7.40–7.42 (1H, m), 7.61 (1H, broad s) IR ν film (cm$^{-1}$): 3360, 3286

FORMULATION EXAMPLES AND TESTS

Next, formulation examples and herbicidal activity tests of herbicides regarding the present invention will be described.

Formulation Example 1 (Wettable powder)

A wettable powder was obtained by sufficiently grinding and mixing 20 parts by weight of Compound No. 1 of the present invention, 2 parts by weight of Neopelex (trade name, made by Kao Corporation; sodium dodecyl benzene sulfonate), 1 part by weight of Neugen EA80 (trade name, made by Daiichi Kogyo Seiyaku Industries, Ltd.; polyoxyethylene nonylphenyl ether), 5 parts by weight of white carbon and 72 parts by weight of diatomaceous earth.

Formulation Example 2 (Wettable powder)

A wettable powder was obtained by sufficiently grinding and mixing 20 parts by weight of Compound No. 2 of the present invention, 2 parts by weight of sodium alkylbenzenesulfonate, 1 part by weight of a polyoxyethylene alkylphenyl ether and 77 parts by weight of Giecrite.

Formulation Example 3 (Wettable powder)

A wettable powder was obtained by thoroughly grinding and mixing 50 parts by weight of Compound No. 10 of the present invention, 5 parts by weight of white carbon, 6 parts by weight of polyoxyethylene alkylphenyl ether ammonium sulfate, 2 parts by weight of sodium lignine sulfonate and 37 parts by weight of diatomaceous earth by the use of a jet-O-mizer (trade name; made by Seishin Enterprise Co., Ltd.).

Formulation Example 4 (Flowable formulation)

A flowable formulation was obtained by adding 91.7 parts by weight of water to 5 parts by weight of Compound No. 1 of the present invention, 2 parts by weight of sodium lignine sulfonate, 0.3 part by weight of xanthane gum and 1 part by weight of a polyoxyethylene alkylaryl ether, mixing them, and then finely grinding the mixture by the use of a sand grinder.

Formulation Example 5 (Flowable formulation)

A flowable formulation was obtained by wet grinding and mixing 30 parts by weight of Compound No. 8 of the present invention and a solution of 10 parts by weight of Sun Ekisu P252 (trade name, Nippon Seishi Co., Ltd.; sodium lignin sulfonate) in 50 parts by weight of water, and then mixing the mixture with a solution of 0.2 part by weight of Kelzan S (trade name, made by Kelco Corp.; xanthan gum) in 9.6 parts by weight of water and 0.2 part by weight of Deltop (trade name, made by Takeda Chemical Industries, Ltd.; organic iodine fungicide).

Formulation Example 6 (Powder)

A powder was obtained by thoroughly grinding and mixing 1 part by weight of Compound No. 3 of the present invention, 0.5 part by weight of Emulgen 910 (trade name, made by Kao Corporation; polyoxyethylene nonylphenyl ether) and 98.5 parts by weight of kaolin clay.

Formulation Example 7 (Powder)

A powder was obtained by mixing and grinding 3 parts by weight of Compound No. 6 of the present invention, 3 parts by weight of sodium lignine sulfonate, 2 parts by weight of a polyoxyethylene alkylaryl ether and 92 parts by weight of clay.

Formulation Example 8 (Dry flowable formulation)

A dry flowable formulation was obtained by mixing 60 parts by weight of finely ground Compound No. 1 of the present invention, 5 parts by weight of a sodium alkylbenzenesulfonate and 35 parts by weight of a polypropylene glycol polyethylene glycol ether.

Formulation Example 9 (Granules)

0.3 part by weight of Compound No. 10 of the present invention, 2 parts by weight of Neopelex (trade name, as described above), 2 parts by weight of Sun Ekisu P252 (trade name, as described above), 72.7 parts by weight of bentonite and 23 parts by weight of talc were thoroughly mixed. A suitable amount of water was added to the resultant mixture to wet the same, followed by extrusion of the mass through a small injection molding machine into pellets. After the pellets were dried at 30°–60° C. in air and then crushed into granules, the granules were then classified by a sifting machine to collect granules of 0.3–2 mm.

Formulation Example 10 (Granules)

0.5 part by weight of Compound No. 4 of the present invention, 2 parts by weight of Gosenol GL-05s (PVA made by Nippon Synthetic Chemical Industry Co., Ltd.), 2 parts by weight of Sun Ekisu P252 (trade name, as described above) and 95.5 parts by weight of clay were thoroughly mixed, and a suitable amount of water was then added to the mixture to wet the same, followed by extrusion of the mass through an injection molding machine into pellets. After the pellets were dried at 60°–90° C. in air and then crushed into granules, the granules were then classified by a sifting machine to collect granules of 0.3–1 mm.

Formulation Example 11 (Emulsion)

An emulsion was obtained by mutually mixing and then dissolving 10 parts by weight of Compound No. 5 of the present invention, 10 parts by weight of Sorpole 800A (trade name, made by Toho Chemical Industries Co., Ltd.; a nonionic/anionic surfactant mixture) and 80 parts by weight of o-xylene.

Formulation Example 12 (Wettable powder)

A wettable powder was obtained by sufficiently grinding and mixing 20 parts by weight of Compound No. 17 of the present invention, 2 parts by weight of sodium alkylbenzenesulfonate, 1 part by weight of a polyoxyethylene alkylphenyl ether and 77 parts by weight of Giecrite.

Formulation Example 13 (Powder)

A powder was obtained by thoroughly grinding and mixing 1 part by weight of Compound No. 18 of the present invention, 0.5 part by weight of Emulgen 910 (trade name, made by Kao Corporation; polyoxyethylene nonylphenyl ether) and 98.5 parts by weight of kaolin clay.

Formulation Example 14 (Wettable powder)

A wettable powder was obtained by sufficiently grinding and mixing 20 parts by weight of Compound No. 26 of the present invention, 2 parts by weight of Neopelex (trade name, made by Kao Corporation; sodium dodecyl benzene sulfonate), 1 part by weight of Neugen EA80 (trade name, made by Daiichi Kogyo Seiyaku Industries, Ltd.; polyoxyethylene nonylphenyl ether), 5 parts by weight of white carbon and 72 parts by weight of diatomaceous earth.

Formulation Example 15 (Flowable formulation)

A flowable formulation was obtained by wet grinding and mixing 30 parts by weight of Compound No. 26 of the present invention and a solution of 10 parts by weight of Sun Ekisu P252 (trade name, as described above) in 50 parts by weight of water, and then mixing the mixture with a solution of 0.2 part by weight of Kelzan S (trade name, made by Kelco Corp.; xanthan gum) in 9.6 parts by weight of water and 0.2 part by weight of Deltop (trade name, made by Takeda Chemical Industries, Ltd.; organic iodine fungicide).

Formulation Example 16 (Powder)

A powder was obtained by mixing and grinding 3 parts by weight of Compound No. 27 of the present invention, 3 parts by weight of sodium lignine sulfonate, 2 parts by weight of a polyoxyethylene alkylaryl ether and 92 parts by weight of clay.

Formulation Example 17 (Dry flowable formulation)

A dry flowable formulation was obtained by mixing 60 parts by weight of finely ground Compound No. 28 of the present invention, 5 parts by weight of a sodium alkylbenzenesulfonate and 35 parts by weight of a polypropylene glycol polyethylene glycol ether.

Formulation Example 18 (Granules)

0.5 part by weight of Compound No. 28 of the present invention, 2 parts by weight of Gosenol GL-05s (PVA made by Nippon Synthetic Chemical Industry Co., Ltd.), 2 parts of Sun Ekisu P252 (trade name, as described above) and 95.5 parts of clay were thoroughly mixed, and a suitable amount of water was then added to the mixture to wet the same, followed by extrusion of the mass through an injection molding machine into pellets. After the pellets were dried at 60°–90° C. in air and then crushed into granules, the granules were then classified by a sifting machine to collect granules of 0.3–1 mm.

Formulation Example 19 (Granules)

0.3 part by weight of Compound No. 29 of the present invention, 2 parts by weight of Neopelex (trade name, as described above), 2 parts by weight of Sun Ekisu P252 (trade name, as described above), 72.7 parts by weight of bentonite and 23 parts by weight of talc were thoroughly mixed. A suitable amount of water was added to the resultant mixture to wet the same, followed by extrusion of the mass through a small injection molding machine into pellets. After the pellets were dried at 30°–60° C. in air and then crushed into granules, the granules were then classified by a sifting machine to collect granules of 0.3–2 mm.

Formulation Example 20 (Emulsion)

An emulsion was obtained by mutually mixing and then dissolving 10 parts by weight of Compound No. 29 of the present invention, 10 parts by weight of Sorpole 800A (trade name, made by Toho Chemical Industries Co., Ltd.; nonionic/anionic surfactant mixture) and 80 parts by weight of o-xylene.

Formulation Example 21 (Wettable powder)

A wettable powder was obtained by sufficiently grinding and mixing 20 parts by weight of Compound No. 40 of the present invention, 2 parts by weight of Neopelex (trade name, made by Kao Corporation; sodium dodecyl benzene sulfonate), 1 part by weight of Neugen EA80 (trade name, made by Daiichi Kogyo Seiyaku Industries, Ltd.; polyoxyethylene nonylphenyl ether), 5 parts by weight of white carbon and 72 parts by weight of diatomaceous earth.

Formulation Example 22 (Granules)

1.5 parts by weight of Compound No. 45 of the present invention, 2 parts by weight of Gosenol GL-05s (PVA made by Nippon Synthetic Chemical Industry Co., Ltd.), 2 parts by weight of Sun Ekisu P252 (trade name, as described above) and 94.5 parts by weight of clay were thoroughly mixed, and a suitable amount of water was then added to the mixture to wet the same, followed by extrusion of the mass through an injection molding machine into pellets. After the pellets were dried at 60°–90° C. in air and then crushed into granules, the granules were then classified by a sifting machine to collect granules of 0.3–1 mm.

Test 1 Treatment of Soil under Submerged Condition (Pre-emergence Treatment)

1/500,000-hectare Wagner pots were filled with soil. Seeds of *Echinochloa crusgalli*, bulrush (*Scirpus juncoides*), monochoria (*Monochoria vaginalis*) and false pimpernel (*Lindernia pyxidaria*) were sown or planted under submerged condition. Two pairs of rice (*Oryza sativa*) seedlings (2–3 leaf stage), which had been reared in advance, were transplanted to each pot and were allowed to grow in a green house. Each pair consisted of two rice seedlings. One day later (before emergence of weeds), each pot was treated with granules which had been prepared by processing a predetermined amount of the test compound in accordance with the procedure described in Formulation Example 9. The growing state of weeds and the injurious state to rice were observed after 30 days from a processing day. The results are summarized in Table 5. In the tables, the damage degree of each test plant and the injurious degree to rice were determined by comparing the dry weight of the test plant and rice with that of the corresponding plant and rice in untreated pots, and they are denoted in accordance with the following standard.

| Rank | Growth rate (%) expressed in terms of the percentage of dry weight relative to the dry weight of untreated group | |
|---|---|---|
| 5 | 0–5 | (Death) |
| 4 | 6–10 | (Severe damages) |
| 3 | 11–40 | (Medium damages) |
| 2 | 41–70 | (Small damages) |
| 1 | 71–90 | (Slight damages) |
| 0 | 91–100 | (No damages) |

Comparative Compounds A, B and C mean the following compounds, respectively (the same shall apply to Test 2).

A: 1,5-dimethyl-3-(3,5-dichlorophenyl)-3-azabicyclo[3.1.0]hexane-2,4-dione (general name: procymidone)

B: 1-phenyl-3-phenylethyl-3-azabicyclo[3.1.0]hexane-2,4-dione

C: 3-ethyl-1-phenyl-3-azabicyclo[3.1.0]hexane-2-one

TABLE 5

| Compound No. | Application rate, kg/ha | *Echinochloa crusgalli* | Monochoria (*Monocholia vaginalis*) | Bulrush (*Scirpus juncoides*) | False pimpernel (*Lindernia pyxidaria*) | Rice (*Oryza sativa*) |
|---|---|---|---|---|---|---|
| 1 | 0.13 | 5 | 5 | 5 | 5 | 0 |
|  | 0.25 | 5 | 5 | 5 | 5 | 0 |
|  | 0.5 | 5 | 5 | 5 | 5 | 1 |
| 2 | 0.13 | 5 | 5 | 5 | 4 | 0 |
|  | 0.25 | 5 | 5 | 5 | 5 | 0 |
|  | 0.5 | 5 | 5 | 5 | 5 | 1 |
| 3 | 0.13 | 5 | 4 | 5 | 5 | 0 |
|  | 0.25 | 5 | 5 | 5 | 5 | 0 |
|  | 0.5 | 5 | 5 | 5 | 5 | 0 |
| 4 | 0.13 | 5 | 4 | 4 | 5 | 0 |
|  | 0.25 | 5 | 5 | 5 | 5 | 0 |
|  | 0.5 | 5 | 5 | 5 | 5 | 0 |
| 5 | 0.13 | 5 | 4 | 4 | 5 | 0 |
|  | 0.25 | 5 | 5 | 5 | 5 | 0 |
|  | 0.5 | 5 | 5 | 5 | 5 | 0 |
| 6 | 0.13 | 5 | 4 | 4 | 4 | 0 |
|  | 0.25 | 5 | 5 | 5 | 5 | 0 |
|  | 0.5 | 5 | 5 | 5 | 5 | 0 |
| 7 | 0.13 | 5 | 4 | 4 | 5 | 0 |
|  | 0.25 | 5 | 5 | 5 | 5 | 0 |
|  | 0.5 | 5 | 5 | 5 | 5 | 1 |
| 8 | 0.13 | 5 | 4 | 3 | 5 | 0 |
|  | 0.25 | 5 | 5 | 4 | 5 | 0 |
|  | 0.5 | 5 | 5 | 5 | 5 | 1 |
| 9 | 0.13 | 5 | 4 | 4 | 5 | 0 |
|  | 0.25 | 5 | 5 | 4 | 5 | 0 |
|  | 0.5 | 5 | 5 | 5 | 5 | 0 |
| 10 | 0.13 | 5 | 5 | 5 | 5 | 0 |
|  | 0.25 | 5 | 5 | 5 | 5 | 0 |
|  | 0.5 | 5 | 5 | 5 | 5 | 0 |
| 11 | 0.13 | 5 | 4 | 4 | 4 | 0 |
|  | 0.25 | 5 | 5 | 5 | 5 | 0 |
|  | 0.5 | 5 | 5 | 5 | 5 | 0 |
| 12 | 0.13 | 5 | 5 | 4 | 5 | 0 |
|  | 0.25 | 5 | 5 | 5 | 5 | 0 |
|  | 0.5 | 5 | 5 | 5 | 5 | 0 |
| 13 | 0.13 | 5 | 4 | 5 | 5 | 0 |
|  | 0.25 | 5 | 5 | 5 | 5 | 0 |
|  | 0.5 | 5 | 5 | 5 | 5 | 0 |
| 14 | 0.13 | 4 | 3 | 4 | 4 | 0 |
|  | 0.25 | 5 | 4 | 4 | 5 | 0 |
|  | 0.5 | 5 | 5 | 5 | 5 | 0 |
| 15 | 0.13 | 4 | 4 | 4 | 3 | 0 |
|  | 0.25 | 5 | 4 | 5 | 4 | 0 |
|  | 0.5 | 5 | 5 | 5 | 5 | 0 |
| 16 | 0.13 | 4 | 5 | 4 | 4 | 0 |
|  | 0.25 | 5 | 5 | 5 | 5 | 0 |
|  | 0.5 | 5 | 5 | 5 | 5 | 0 |
| 17 | 0.13 | 5 | 4 | 4 | 4 | 0 |
|  | 0.25 | 5 | 5 | 5 | 5 | 0 |
|  | 0.5 | 5 | 5 | 5 | 5 | 0 |

TABLE 5-continued

| Compound No. | Application rate, kg/ha | Echinochloa crusgalli | Monochoria (Monocholia vaginalis) | Bulrush (Scirpus juncoides) | False pimpernel (Lindernia pyxidaria) | Rice (Oryza sativa) |
|---|---|---|---|---|---|---|
| 18 | 0.13 | 5 | 4 | 5 | 4 | 0 |
|  | 0.25 | 5 | 5 | 5 | 5 | 0 |
|  | 0.5 | 5 | 5 | 5 | 5 | 1 |
| 19 | 0.13 | 5 | 4 | 5 | 5 | 0 |
|  | 0.25 | 5 | 5 | 5 | 5 | 0 |
|  | 0.5 | 5 | 5 | 5 | 5 | 0 |
| 20 | 0.13 | 4 | 3 | 3 | 4 | 0 |
|  | 0.25 | 5 | 5 | 4 | 5 | 0 |
|  | 0.5 | 5 | 5 | 5 | 5 | 0 |
| 21 | 0.13 | 3 | 3 | 3 | 4 | 0 |
|  | 0.25 | 4 | 4 | 4 | 5 | 0 |
|  | 0.5 | 5 | 5 | 5 | 5 | 0 |
| 22 | 0.13 | 4 | 3 | 4 | 3 | 0 |
|  | 0.25 | 5 | 4 | 5 | 4 | 0 |
|  | 0.5 | 5 | 5 | 5 | 5 | 0 |
| 23 | 0.13 | 4 | 3 | 3 | 4 | 0 |
|  | 0.25 | 5 | 4 | 4 | 5 | 0 |
|  | 0.5 | 5 | 5 | 5 | 5 | 0 |
| 24 | 0.13 | 5 | 4 | 4 | 4 | 0 |
|  | 0.25 | 5 | 5 | 5 | 5 | 0 |
|  | 0.5 | 5 | 5 | 5 | 5 | 0 |
| 25 | 0.13 | 5 | 4 | 5 | 4 | 0 |
|  | 0.25 | 5 | 5 | 5 | 5 | 0 |
|  | 0.5 | 5 | 5 | 5 | 5 | 0 |
| 26 | 0.13 | 5 | 5 | 5 | 5 | 0 |
|  | 0.25 | 5 | 5 | 5 | 5 | 0 |
|  | 0.5 | 5 | 5 | 5 | 5 | 1 |
| 27 | 0.13 | 5 | 5 | 5 | 5 | 0 |
|  | 0.25 | 5 | 5 | 5 | 5 | 0 |
|  | 0.5 | 5 | 5 | 5 | 5 | 1 |
| 28 | 0.13 | 5 | 5 | 5 | 5 | 0 |
|  | 0.25 | 5 | 5 | 5 | 5 | 0 |
|  | 0.5 | 5 | 5 | 5 | 5 | 0 |
| 29 | 0.13 | 5 | 5 | 5 | 5 | 0 |
|  | 0.25 | 5 | 5 | 5 | 5 | 0 |
|  | 0.5 | 5 | 5 | 5 | 5 | 0 |
| 30 | 0.13 | 5 | 4 | 5 | 4 | 0 |
|  | 0.25 | 5 | 5 | 5 | 5 | 0 |
|  | 0.5 | 5 | 5 | 5 | 5 | 0 |
| 31 | 0.13 | 4 | 4 | 4 | 4 | 0 |
|  | 0.25 | 5 | 5 | 4 | 5 | 0 |
|  | 0.5 | 5 | 5 | 5 | 5 | 1 |
| 32 | 0.13 | 4 | 4 | 5 | 4 | 0 |
|  | 0.25 | 4 | 4 | 5 | 4 | 0 |
|  | 0.5 | 5 | 5 | 5 | 5 | 0 |
| 33 | 0.13 | 4 | 3 | 4 | 4 | 0 |
|  | 0.25 | 5 | 4 | 5 | 5 | 0 |
|  | 0.5 | 5 | 5 | 5 | 5 | 1 |
| 34 | 0.13 | 5 | 5 | 5 | 5 | 0 |
|  | 0.25 | 5 | 5 | 5 | 5 | 0 |
|  | 0.5 | 5 | 5 | 5 | 5 | 0 |
| 35 | 0.13 | 4 | 4 | 5 | 5 | 0 |
|  | 0.25 | 5 | 5 | 5 | 5 | 0 |
|  | 0.5 | 5 | 5 | 5 | 5 | 0 |
| 36 | 0.13 | 4 | 4 | 5 | 4 | 0 |
|  | 0.25 | 5 | 5 | 5 | 5 | 0 |
|  | 0.5 | 5 | 5 | 5 | 5 | 1 |
| 37 | 0.13 | 5 | 5 | 5 | 5 | 0 |
|  | 0.25 | 5 | 5 | 5 | 5 | 0 |
|  | 0.5 | 5 | 5 | 5 | 5 | 0 |
| 38 | 0.13 | 4 | 4 | 4 | 5 | 0 |
|  | 0.25 | 5 | 5 | 5 | 5 | 0 |
|  | 0.5 | 5 | 5 | 5 | 5 | 1 |
| 39 | 0.13 | 4 | 4 | 4 | 4 | 0 |
|  | 0.25 | 5 | 5 | 5 | 5 | 0 |
|  | 0.5 | 5 | 5 | 5 | 5 | 0 |
| 40 | 0.13 | 5 | 5 | 5 | 5 | 0 |
|  | 0.25 | 5 | 5 | 5 | 5 | 0 |
|  | 0.5 | 5 | 5 | 5 | 5 | 0 |
| 41 | 0.13 | 5 | 5 | 5 | 5 | 0 |
|  | 0.25 | 5 | 5 | 5 | 5 | 0 |
|  | 0.5 | 5 | 5 | 5 | 5 | 1 |
| 42 | 0.13 | 5 | 5 | 5 | 5 | 0 |
|  | 0.25 | 5 | 5 | 5 | 5 | 0 |
|  | 0.5 | 5 | 5 | 5 | 5 | 1 |
| 43 | 0.13 | 5 | 4 | 5 | 4 | 1 |
|  | 0.25 | 5 | 5 | 5 | 5 | 0 |
|  | 0.5 | 5 | 5 | 5 | 5 | 0 |

TABLE 5-continued

| Compound No. | Application rate, kg/ha | Echinochloa crusgalli | Monochoria (Monocholia vaginalis) | Bulrush (Scirpus juncoides) | False pimpernel (Lindernia pyxidaria) | Rice (Oryza sativa) |
|---|---|---|---|---|---|---|
| 44 | 0.13 | 5 | 5 | 5 | 5 | 1 |
|  | 0.25 | 5 | 5 | 5 | 5 | 0 |
|  | 0.5 | 5 | 5 | 5 | 5 | 0 |
| 45 | 0.13 | 5 | 5 | 5 | 5 | 1 |
|  | 0.25 | 5 | 5 | 5 | 5 | 0 |
|  | 0.5 | 5 | 5 | 5 | 5 | 0 |
| A | 0.13 | 0 | 0 | 0 | 0 | 0 |
|  | 0.25 | 0 | 0 | 0 | 0 | 0 |
|  | 0.5 | 0 | 0 | 0 | 0 | 0 |
| B | 0.13 | 0 | 0 | 0 | 0 | 0 |
|  | 0.25 | 0 | 0 | 0 | 0 | 0 |
|  | 0.5 | 0 | 0 | 0 | 0 | 0 |
| C | 0.13 | 0 | 0 | 0 | 0 | 0 |
|  | 0.25 | 0 | 0 | 0 | 0 | 0 |
|  | 0.5 | 0 | 0 | 0 | 0 | 0 |

In these tests, the herbicidal compositions regarding the present invention exerted high herbicidal effects to the sample weeds in the paddy fields in spite of the low application rates, and they also exerted excellent safety to the rice. Compounds A, B and C scarcely exhibited the herbicidal effect.

Test 2 Treatment of Soil under Submerged Condition (Growing Period Treatment)

1/500,000-hectare Wagner pots were filled with soil. Seeds of *Echinochloa crusgalli*, bulrush (*Scirpus juncoides*), monochoria (*Monochoria vaginalis*) and false pimpernel (*Lindernia pyxidaria*) were sown under submerged condition. Two pairs of rice (*Oryza sativa*) seedlings (2-3 leaf stage), which had been reared in advance, were transplanted to each pot and were allowed to grow in a green house. Each pair consisted of two rice seedlings. When *Echinochloa crusgalli* became unifoliate, each pot was treated with granules which had been prepared by processing a predetermined amount of the test compound in accordance with the procedure described in Formulation Example 10. The emergence state of weeds and the injurious state to rice were observed after 30 days from the processing day. The results are summarized in Table 6. In the table, the damage degree of each test plant and the injurious degree to rice were determined in the same manner as in Test 1.

TABLE 6

| Compound No. | Application rate, kg/ha | Echinochloa crusgalli | Monochoria (Monocholia vaginalis) | Bulrush (Scirpus juncoides) | False pimpernel (Lindernia pyxidaria) | Rice (Oryza sativa) |
|---|---|---|---|---|---|---|
| 1 | 0.25 | 5 | 5 | 5 | 5 | 0 |
|  | 0.5 | 5 | 5 | 5 | 5 | 0 |
|  | 1.0 | 5 | 5 | 5 | 5 | 1 |
| 2 | 0.25 | 5 | 4 | 5 | 4 | 0 |
|  | 0.5 | 5 | 5 | 5 | 5 | 0 |
|  | 1.0 | 5 | 5 | 5 | 5 | 0 |
| 3 | 0.25 | 4 | 4 | 5 | 4 | 0 |
|  | 0.5 | 5 | 5 | 5 | 5 | 0 |
|  | 1.0 | 5 | 5 | 5 | 5 | 0 |
| 4 | 0.25 | 4 | 3 | 3 | 5 | 0 |
|  | 0.5 | 5 | 4 | 4 | 5 | 0 |
|  | 1.0 | 5 | 5 | 5 | 5 | 0 |
| 5 | 0.25 | 4 | 3 | 3 | 5 | 0 |
|  | 0.5 | 5 | 4 | 4 | 5 | 0 |
|  | 1.0 | 5 | 5 | 5 | 5 | 0 |
| 6 | 0.25 | 4 | 3 | 2 | 5 | 0 |
|  | 0.5 | 5 | 4 | 3 | 5 | 0 |
|  | 1.0 | 5 | 5 | 5 | 5 | 0 |
| 7 | 0.25 | 5 | 4 | 3 | 5 | 0 |
|  | 0.5 | 5 | 5 | 4 | 5 | 0 |
|  | 1.0 | 5 | 5 | 5 | 5 | 1 |
| 8 | 0.25 | 5 | 4 | 3 | 4 | 0 |
|  | 0.5 | 5 | 5 | 4 | 5 | 0 |
|  | 1.0 | 5 | 5 | 5 | 5 | 1 |
| 9 | 0.25 | 5 | 4 | 2 | 4 | 0 |
|  | 0.5 | 5 | 5 | 3 | 5 | 0 |
|  | 1.0 | 5 | 5 | 5 | 5 | 1 |
| 10 | 0.25 | 5 | 5 | 5 | 5 | 0 |
|  | 0.5 | 5 | 5 | 5 | 5 | 0 |
|  | 1.0 | 5 | 5 | 5 | 5 | 0 |
| 11 | 0.25 | 5 | 4 | 3 | 5 | 0 |
|  | 0.5 | 5 | 4 | 5 | 5 | 0 |
|  | 1.0 | 5 | 5 | 5 | 5 | 0 |
| 12 | 0.25 | 5 | 4 | 3 | 5 | 0 |
|  | 0.5 | 5 | 5 | 5 | 5 | 0 |
|  | 1.0 | 5 | 5 | 5 | 5 | 0 |
| 13 | 0.25 | 5 | 4 | 5 | 4 | 0 |

TABLE 6-continued

| Compound No. | Application rate, kg/ha | Echinochloa crusgalli | Monochoria (Monocholia vaginalis) | Bulrush (Scirpus juncoides) | False pimpernel (Lindernia pyxidaria) | Rice (Oryza sativa) |
|---|---|---|---|---|---|---|
| | 0.5 | 5 | 5 | 5 | 5 | 0 |
| | 1.0 | 5 | 5 | 5 | 5 | 0 |
| 14 | 0.25 | 4 | 3 | 5 | 4 | 0 |
| | 0.5 | 5 | 4 | 5 | 5 | 0 |
| | 1.0 | 5 | 5 | 5 | 5 | 1 |
| 15 | 0.25 | 4 | 4 | 4 | 4 | 0 |
| | 0.5 | 5 | 5 | 5 | 5 | 0 |
| | 1.0 | 5 | 5 | 5 | 5 | 0 |
| 16 | 0.25 | 5 | 5 | 5 | 4 | 0 |
| | 0.5 | 5 | 5 | 5 | 5 | 0 |
| | 1.0 | 5 | 5 | 5 | 5 | 1 |
| 17 | 0.25 | 5 | 4 | 5 | 5 | 0 |
| | 0.5 | 5 | 5 | 5 | 5 | 0 |
| | 1.0 | 5 | 5 | 5 | 5 | 1 |
| 18 | 0.25 | 5 | 4 | 5 | 5 | 0 |
| | 0.5 | 5 | 5 | 5 | 5 | 0 |
| | 1.0 | 5 | 5 | 5 | 5 | 1 |
| 19 | 0.25 | 5 | 4 | 5 | 4 | 0 |
| | 0.5 | 5 | 5 | 5 | 5 | 0 |
| | 1.0 | 5 | 5 | 5 | 5 | 1 |
| 20 | 0.25 | 4 | 3 | 5 | 3 | 0 |
| | 0.5 | 5 | 4 | 5 | 4 | 0 |
| | 1.0 | 5 | 5 | 5 | 5 | 0 |
| 21 | 0.25 | 4 | 3 | 5 | 4 | 0 |
| | 0.5 | 5 | 4 | 5 | 5 | 0 |
| | 1.0 | 5 | 5 | 5 | 5 | 0 |
| 22 | 0.25 | 4 | 3 | 3 | 3 | 0 |
| | 0.5 | 5 | 4 | 4 | 4 | 0 |
| | 1.0 | 5 | 5 | 5 | 5 | 0 |
| 23 | 0.25 | 4 | 3 | 4 | 3 | 0 |
| | 0.5 | 5 | 4 | 5 | 4 | 0 |
| | 1.0 | 5 | 5 | 5 | 5 | 0 |
| 24 | 0.25 | 5 | 4 | 4 | 4 | 0 |
| | 0.5 | 5 | 5 | 5 | 5 | 0 |
| | 1.0 | 5 | 5 | 5 | 5 | 0 |
| 25 | 0.25 | 4 | 4 | 4 | 4 | 0 |
| | 0.5 | 5 | 5 | 5 | 5 | 0 |
| | 1.0 | 5 | 5 | 5 | 5 | 0 |
| 26 | 0.25 | 5 | 5 | 5 | 5 | 0 |
| | 0.5 | 5 | 5 | 5 | 5 | 0 |
| | 1.0 | 5 | 5 | 5 | 5 | 1 |
| 27 | 0.25 | 5 | 5 | 5 | 5 | 0 |
| | 0.5 | 5 | 5 | 5 | 5 | 0 |
| | 1.0 | 5 | 5 | 5 | 5 | 1 |
| 28 | 0.25 | 5 | 5 | 5 | 5 | 0 |
| | 0.5 | 5 | 5 | 5 | 5 | 0 |
| | 1.0 | 5 | 5 | 5 | 5 | 0 |
| 29 | 0.25 | 5 | 5 | 5 | 5 | 0 |
| | 0.5 | 5 | 5 | 5 | 5 | 0 |
| | 1.0 | 5 | 5 | 5 | 5 | 0 |
| 30 | 0.25 | 5 | 4 | 4 | 4 | 0 |
| | 0.5 | 5 | 5 | 5 | 5 | 0 |
| | 1.0 | 5 | 5 | 5 | 5 | 0 |
| 31 | 0.25 | 4 | 3 | 4 | 4 | 0 |
| | 0.5 | 5 | 4 | 5 | 5 | 0 |
| | 1.0 | 5 | 5 | 5 | 5 | 1 |
| 32 | 0.25 | 4 | 3 | 4 | 3 | 0 |
| | 0.5 | 5 | 4 | 5 | 4 | 0 |
| | 1.0 | 5 | 5 | 5 | 5 | 1 |
| 33 | 0.25 | 3 | 3 | 4 | 4 | 0 |
| | 0.5 | 4 | 4 | 5 | 5 | 0 |
| | 1.0 | 5 | 5 | 5 | 5 | 0 |
| 34 | 0.25 | 5 | 5 | 5 | 5 | 0 |
| | 0.5 | 5 | 5 | 5 | 5 | 0 |
| | 1.0 | 5 | 5 | 5 | 5 | 0 |
| 35 | 0.25 | 5 | 5 | 5 | 5 | 0 |
| | 0.5 | 5 | 5 | 5 | 5 | 0 |
| | 1.0 | 5 | 5 | 5 | 5 | 0 |
| 36 | 0.25 | 4 | 3 | 4 | 4 | 0 |
| | 0.5 | 5 | 4 | 5 | 5 | 0 |
| | 1.0 | 5 | 5 | 5 | 5 | 0 |
| 37 | 0.25 | 5 | 5 | 5 | 5 | 0 |
| | 0.5 | 5 | 5 | 5 | 5 | 0 |
| | 1.0 | 5 | 5 | 5 | 5 | 0 |
| 38 | 0.25 | 3 | 3 | 5 | 4 | 0 |
| | 0.5 | 4 | 4 | 5 | 5 | 0 |
| | 1.0 | 5 | 5 | 5 | 5 | 0 |
| 39 | 0.25 | 3 | 3 | 4 | 4 | 0 |

TABLE 6-continued

| Compound No. | Application rate, kg/ha | Echinochloa crusgalli | Monochoria (Monocholia vaginalis) | Bulrush (Scirpus juncoides) | False pimpernel (Lindernia pyxidaria) | Rice (Oryza sativa) |
|---|---|---|---|---|---|---|
|  | 0.5 | 4 | 4 | 5 | 5 | 0 |
|  | 1.0 | 5 | 5 | 5 | 5 | 0 |
| 40 | 0.25 | 5 | 5 | 5 | 5 | 0 |
|  | 0.5 | 5 | 5 | 5 | 5 | 0 |
|  | 1.0 | 5 | 5 | 5 | 5 | 0 |
| 41 | 0.25 | 5 | 5 | 5 | 5 | 0 |
|  | 0.5 | 5 | 5 | 5 | 5 | 0 |
|  | 1.0 | 5 | 5 | 5 | 5 | 0 |
| 42 | 0.25 | 5 | 4 | 4 | 5 | 0 |
|  | 0.5 | 5 | 5 | 5 | 5 | 0 |
|  | 1.0 | 5 | 5 | 5 | 5 | 0 |
| 43 | 0.25 | 5 | 4 | 4 | 4 | 0 |
|  | 0.5 | 5 | 5 | 5 | 5 | 0 |
|  | 1.0 | 5 | 5 | 5 | 5 | 0 |
| 44 | 0.25 | 5 | 5 | 5 | 5 | 1 |
|  | 0.5 | 5 | 5 | 5 | 5 | 0 |
|  | 1.0 | 5 | 5 | 5 | 5 | 0 |
| 45 | 0.25 | 5 | 5 | 5 | 5 | 1 |
|  | 0.5 | 5 | 5 | 5 | 5 | 0 |
|  | 1.0 | 5 | 5 | 5 | 5 | 0 |
| A | 0.25 | 0 | 0 | 0 | 0 | 0 |
|  | 0.5 | 0 | 0 | 0 | 0 | 0 |
|  | 1.0 | 0 | 0 | 0 | 0 | 0 |
| B | 0.25 | 0 | 0 | 0 | 0 | 0 |
|  | 0.5 | 0 | 0 | 0 | 0 | 0 |
|  | 1.0 | 0 | 0 | 0 | 0 | 0 |
| C | 0.25 | 0 | 0 | 0 | 0 | 0 |
|  | 0.5 | 0 | 0 | 0 | 0 | 0 |
|  | 1.0 | 0 | 0 | 0 | 0 | 0 |

In these tests, the herbicidal compositions regarding the present invention exerted high herbicidal effects to the sample weeds in the paddy fields in spite of the low application rates, and they also exerted excellent safety to the rice. Compounds A, B and C did not exhibit the herbicidal effect at all.

The present invention has some functional effects. That is, 3-azabicyclo[3.1.0]hexane-2-one derivatives represented by the formula (I) regarding the present invention are novel compounds, and a herbicidal composition containing the compound of the present invention shows a herbicidal activity to various weeds in paddy fields in a low application rate in the long term of from the pre-emergence of weeds to the growing period of the developed weeds. On the other hand, the herbicidal composition does not show the herbicidal activity to rice (Oryza sativa). That is, it has an excellent selectivity, and so it can be safely used.

What is claimed is:

1. A 3-azabicyclo[3.1.0]hexane-2-one derivative represented by the formula (I)

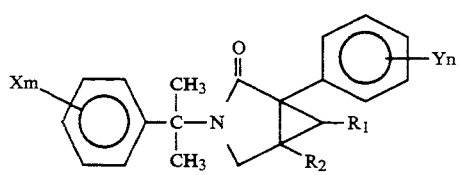

(I)

wherein X is a halogen atom, an alkyl group having 1 to 3 carbon atoms, an alkoxy group having 1 to 3 carbon atoms or a haloalkyl group having 1 to 3 carbon atoms; Y is a halogen atom or an alkyl group having 1 to 3 carbon atoms; $R_1$ is a hydrogen atom or an alkyl group having 1 to 3 carbon atoms; $R_2$ is a hydrogen atom or an alkyl group having 1 to 3 carbon atoms; m is an integer of 0 to 3; n is an integer of 0 to 2; and when m is 2 or 3, the groups represented by X may be identical or different, and when n is 2, the groups represented by Y may be identical or different.

2. The compound according to claim 1 wherein $R_1$ is a hydrogen atom and $R_2$ is a methyl group.

3. The compound according to claim 2 wherein one of the groups represented by X is a halogen atom substituted at the 3-position.

4. The compound according to claim 2 wherein Yn is a fluorine atom substituted at the 2-position.

5. The compound according to claim 3 wherein Yn is a fluorine atom substituted at the 2-position.

6. A herbicidal composition comprising a 3-azabicyclo[3.1.0]hexane-2-one derivative represented by the formula (I)

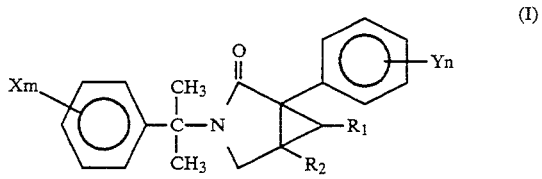

(I)

wherein X is a halogen atom, an alkyl group having 1 to 3 carbon atoms, an alkoxy group having 1 to 3 carbon atoms or a haloalkyl group having 1 to 3 carbon atoms; Y is a halogen atom or an alkyl group having 1 to 3 carbon atoms; $R_1$ is a hydrogen atom or an alkyl group having 1 to 3 carbon atoms; $R_2$ is a hydrogen atom or an alkyl group having 1 to 3 carbon atoms; m is an integer of 0 to 3; n is an integer of 0 to 2; and when m is 2 or 3, the groups represented by X may be identical or different, and when n is 2, the groups represented by Y may be identical or different.

7. The herbicidal composition according to claim 6 wherein $R_1$ is a hydrogen atom and $R_2$ is a methyl group.

8. The herbicidal composition according to claim 7 wherein one of the groups represented by X is a halogen atom substituted at the 3-position.

9. The herbicidal composition according to claim 7 wherein Yn is a fluorine atom substituted at the 2-position.

10. The herbicidal composition according to claim 8 wherein Yn is a fluorine atom substituted at the 2-position.

* * * * *